US011071452B2

United States Patent
Satake et al.

(10) Patent No.: US 11,071,452 B2
(45) Date of Patent: Jul. 27, 2021

(54) OPTICAL COHERENCE TOMOGRAPHY DEVICE, OPTICAL COHERENCE TOMOGRAPHY CALCULATION METHOD, AND OPTICAL COHERENCE TOMOGRAPHY CALCULATION PROGRAM

(71) Applicant: NIDEK CO., LTD., Aichi (JP)

(72) Inventors: Norimasa Satake, Aichi (JP); Yukihiro Higuchi, Toyota (JP); Yuji Murase, Aichi (JP); Yasuhiro Furuuchi, Aichi (JP); Hajime Namiki, Aichi (JP); Naoki Isogai, Aichi (JP); Masaaki Hanebuchi, Aichi (JP); Naoki Takeno, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/753,927

(22) Filed: Jun. 29, 2015

(65) Prior Publication Data

US 2015/0374228 A1 Dec. 31, 2015

(30) Foreign Application Priority Data

Jun. 30, 2014 (JP) .............................. JP2014-135022
Jun. 30, 2014 (JP) .............................. JP2014-135023
Jun. 30, 2014 (JP) .............................. JP2014-135024

(51) Int. Cl.
*A61B 3/10* (2006.01)
*G06T 7/00* (2017.01)

(52) U.S. Cl.
CPC ............ *A61B 3/102* (2013.01); *G06T 7/0016* (2013.01); *G06T 2207/10101* (2013.01); *G06T 2207/30041* (2013.01)

(58) Field of Classification Search
CPC ... A61B 3/0025; A61B 3/0033; A61B 3/0041; A61B 3/0058; A61B 3/0091; A61B 3/10;
(Continued)

(56) References Cited

U.S. PATENT DOCUMENTS 7,301,644 B2 11/2007 Knighton et al.
2008/0100612 A1 5/2008 Dastmalchi et al.
(Continued)

FOREIGN PATENT DOCUMENTS

JP 2010-249740 A 11/2010
JP 2013-154121 A 8/2013
(Continued)

OTHER PUBLICATIONS

Communication dated Oct. 31, 2017, from the Japanese Patent Office in counterpart application No. 2014-135024.
(Continued)

*Primary Examiner* — Jie Lei
(74) *Attorney, Agent, or Firm* — Sughrue Mion, PLLC

(57) ABSTRACT

The present disclosure relates to an optical coherence tomography (OCT) including: an OCT device, an OCT calculation method, and an OCT calculation program, enabling correlation between images to be easily performed; more specifically it relates to a case where a functional OCT image such as a motion contrast is acquired by using the OCT; acquiring the functional OCT image through a calculation process of an OCT signal is a time-consuming process, for this reason, a long time elapses until the point that a functional OCT image can be observed after OCT imaging is completed, and thus this causes stress to a subject and an examiner; the present disclosure provides an OCT device, an OCT calculation method, and an OCT calculation program, enabling a functional OCT image to be rapidly acquired and enables an examiner to easily perform diagnosis.

21 Claims, 9 Drawing Sheets

(58) Field of Classification Search
CPC ..... A61B 3/1005; A61B 3/102; A61B 3/1025;
A61B 3/113; A61B 3/12; A61B 3/1125;
A61B 3/1233; A61B 3/1241; A61B 3/14;
A61B 3/145; A61B 3/14555; A61B
3/152; A61B 3/18; A61B 5/0059; A61B
5/0062; A61B 5/0066; A61B 5/0068;
A61B 5/0261; A61B 5/7257; A61B
2560/0475; A61B 2562/0233; G01B
9/02019; G01B 9/02027; G01B 9/0201;
G01B 9/02028; G01B 9/0203; G01B
9/02044; G01B 9/02064; G01B 9/0207;
G01B 9/02083; G01B 9/02084; G01B
9/02085; G01B 9/02087; G01B 9/02088;
G01B 9/02089; G01B 9/02091; G01B
9/02004; G01B 2290/45; G01B 2290/60;
G01B 2290/65; G06T 7/0014; G06T
7/0016; G06T 7/002; G06T 7/0022; G06T
7/0024; G06T 7/0026; G06T 7/0028;
G06T 7/003; G06T 7/0032; G06T 7/0042;
G06T 7/0065; G06T 7/0075; G06T
7/0097; G06T 7/2006; G06T 7/2033;
G06T 7/204; G06T 19/00; G06T
2207/10016; G06T 2207/10072; G06T
2207/10101; G06T 2207/20068; G06T
2207/30004; G06T 2207/30041; G06T
2207/30101; G06K 9/0061; G06K
9/6203; G06K 9/6204; G06K 9/6878;
G01N 21/41; G01N 21/4795; G01N
21/08
USPC ........ 351/205–206, 208–210, 212, 221, 246;
356/450, 477, 479, 495, 497; 382/103,
382/131, 151; 250/363.04; 348/78;
345/440; 600/425; 702/155
See application file for complete search history.

(56) References Cited

U.S. PATENT DOCUMENTS

| | | |
|---|---|---|
| 2011/0034803 A1 | 2/2011 | Stetson |
| 2012/0113390 A1* | 5/2012 | Torii ..................... A61B 3/024 351/208 |
| 2012/0120408 A1 | 5/2012 | Yasuno et al. |
| 2012/0277579 A1 | 11/2012 | Sharma et al. |
| 2013/0176532 A1* | 7/2013 | Sharma ................. A61B 3/102 351/206 |
| 2013/0301008 A1 | 11/2013 | Srivastava et al. |
| 2015/0223685 A1 | 8/2015 | Morishima et al. |
| 2016/0317029 A1 | 11/2016 | Srivastava et al. |

FOREIGN PATENT DOCUMENTS

| | | |
|---|---|---|
| JP | 2014-87581 A | 5/2014 |
| JP | 2015-515894 A | 6/2015 |
| WO | 2010143601 A1 | 12/2010 |
| WO | 2013/167641 A1 | 11/2013 |
| WO | 2014/043378 A1 | 3/2014 |

OTHER PUBLICATIONS

Kim et al., "Noninvasive Imaging of the Foveal Avascular Zone with High-Speed, Phase-Variance Optical Coherence Tomography", Investigative Ophthalmology & Visual Science, 53(1) (21 Pages Total), (2012), doi:10.1167/iovs.11-8249.

Communication dated Feb. 19, 2019, from the Japanese Patent Office in counterpart application No. 2014-135022.

Communication dated May 2, 2018 issued by the Japanese Patent Office in counterpart Japanese Patent Application No. 2014-135023.

Communication dated May 2, 2018 issued by the Japanese Patent Office in counterpart Japanese Patent Application No. 2014-135024.

Communication dated May 8, 2018 issued by the Japanese Patent Office in counterpart Japanese Patent Application No. 2014-135022.

* cited by examiner

OPTICAL COHERENCE TOMOGRAPHY DEVICE, OPTICAL COHERENCE TOMOGRAPHY CALCULATION METHOD, AND OPTICAL COHERENCE TOMOGRAPHY CALCULATION PROGRAM

CROSS REFERENCE TO RELATED APPLICATIONS

This application is based upon and claims the benefit of priorities of Japanese Patent Application No. 2014-135022 filed on Jun. 30, 2014, Japanese Patent Application No. 2014-135023 filed on Jun. 30, 2014 and Japanese Patent Application No. 2014-135024 filed on Jun. 30, 2014, the contents of which are incorporated herein by reference in its entirety.

TECHNICAL FIELD

The present invention relates to an optical coherence tomography device, an optical coherence tomography calculation method, and an optical coherence tomography calculation program for obtaining motion contrast data of a test substance.

BACKGROUND

In the related art, as a device for angiography, for example, a fundus camera or a scanning laser optometric device is known. In this case, a contrast agent which emits light in response to specific excitation light is injected into a body. The device obtains an angiographic image by receiving light from the contrast agent. In other words, in the related art, injection of the contrast agent is necessary. In recent years, a device has been proposed in which a motion contrast (a pseudo-angiographic image) is obtained by applying an OCT technique without using a contrast agent (for example, refer to WO2010/143601).

In addition, in the related art, a lesion or the like is diagnosed by referring to the angiographic image acquired in the above-described way and to other fundus images.

SUMMARY

The present disclosure relates to an optical coherence tomography device and correlating separately acquired images such as the angiographic image and other fundus images with each other which may be difficult for an inexperienced examiner to perform a diagnosis.

A first aspect of the present disclosure provides an optical coherence tomography device, an optical coherence tomography calculation method, and an optical coherence tomography calculation program, enabling correlation between images to be easily performed.

In addition, in a case where a functional OCT image such as a motion contrast is acquired by using the OCT, a long period of time is required to acquire the functional OCT image through a calculation process of an OCT signal. For this reason, a long time elapses until the point that a functional OCT image can be observed after OCT imaging is completed, and thus this causes stress to a subject and an examiner.

A second aspect of the present disclosure provides an optical coherence tomography device, an optical coherence tomography calculation method, and an optical coherence tomography calculation program, enabling a functional OCT image to be rapidly acquired.

Further, an image such as a motion contrast using the OCT may possibly contribute to supporting diagnosis performed by an examiner. Still further, a method of using an image such as an acquired motion contrast will become important in the future.

A third aspect of the present disclosure provides an optical coherence tomography device and an optical coherence tomography calculation program, enabling an examiner to easily perform diagnosis.

In order to solve the above-described problems, the present disclosure is characterized in having the following configurations.

(1) An optical coherence tomography device comprising:
   a processor; and
   a memory storing a computer program, when executed by the processor, causing the optical coherence tomography device to perform:
   an acquisition instruction of acquiring a plurality of OCT signals which are temporally different from each other with respect to the same position on a test substance, at a plurality of positions on the test substance;
   a calculation instruction of processing the plurality of OCT signals acquired at the plurality of positions on the test substance so as to acquire three-dimensional functional OCT image data of the test substance, and processing at least one of the acquired OCT signal at each of the plurality of positions on the test substance so as to acquire reference enface image data of the test substance;
   an image processing instruction of matching enface image data which is acquired by an enface image acquisition unit configured to acquire enface image data of the test substance with the reference enface image data, so as to correlate the enface image data with the three-dimensional functional OCT image data.

(2) The optical coherence tomography device according to (1),
   wherein the image processing instruction correlates the enface image data with the three-dimensional functional OCT image data so as to superimpose display indicating the three-dimensional functional OCT image data on the enface image data.

(3) The optical coherence tomography device according to (1),
   wherein the image processing instruction acquires two-dimensional OCT functional enface image data which is the enface image data in a predetermined depth region of the test substance based on the three-dimensional functional OCT image data, and correlates the enface image data with the three-dimensional functional OCT image data so as to superimpose display indicating the two-dimensional OCT functional enface image data on the enface image data.

(4) The optical coherence tomography device according to (1),
   wherein the reference enface image data is OCT enface image data which is acquired based on at least one of the plurality of OCT signals acquired at the plurality of positions on the test substance.

(5) The optical coherence tomography device according to (1), wherein
   the computer program, when executed by the processor, further causes the optical coherence tomography device to perform:
   a selection instruction of selecting, based on the enface image data, at least one of OCT enface image data and OCT functional enface image data as the reference enface image data to be correlated with the enface image data, the OCT enface image data being acquired based on at least one of the plurality of OCT signals acquired at the plurality of positions on the test substance, and the OCT functional enface image data being acquired by the image processing unit based on the three-dimensional functional OCT image data, wherein the image processing instruction detects a positional deviation between said at least one of the OCT enface image data and the OCT functional enface image data, selected by the selection instruction, and the enface image data, and correlating the enface image data with the three-dimensional functional OCT image data based on the positional deviation.

(6) The optical coherence tomography device according to (1), wherein the calculation processing instruction performs an adding process on the plurality of OCT signals acquired at each of the plurality of positions on the test substance so as to acquire image data having undergone the adding process at the plurality of positions on the test substance.

(7) The optical coherence tomography device according to (1), wherein the image processing instruction matches the enface image data with the reference enface image data based on at least one of fixation position information and scanning position information.

(8) The optical coherence tomography device according to (1), wherein the OCT signal acquisition instruction acquires the plurality of OCT signals at a first position on the test substance and then acquires the plurality of OCT signals at a second position which is different from the first position, and wherein the first calculation processing instruction processes the plurality of OCT signals acquired at the first position so as to acquire motion contrast data at the first position while the OCT signal acquisition acquires the plurality of OCT signals at either or both of the first position and the second position.

(9) The optical coherence tomography device according to (8), wherein the first position is a first crossing position, and the second position is a second crossing position, and wherein the calculation instruction processes the plurality of OCT signals acquired at the first crossing position so as to acquire motion contrast data at the first crossing position while the plurality of OCT signals are acquired at either or both of the first crossing position and the second crossing position.

(10) The optical coherence tomography device according to (9), wherein the OCT signal acquiring instruction scans, with measurement light, a plurality of different crossing positions of the test substance so as to acquire the OCT signal for acquiring three-dimensional motion contrast data regarding XY directions, and wherein the calculation instruction processes OCT signals at the plurality of crossing positions so as to acquire the three-dimensional motion contrast data.

(11) The optical coherence tomography device according to (9), wherein the OCT signal acquiring instruction scans, with measurement light, a plurality of different crossing positions of the test substance so as to acquire the OCT signal for acquiring three-dimensional motion contrast data regarding XY directions, wherein the calculation instruction processes the OCT signals at the plurality of crossing positions so as to acquire the three-dimensional motion contrast data, wherein the calculation instruction sequentially acquires motion contrast data at the plurality of crossing positions, and wherein the computer program, when executed by the processor, further causes the optical coherence tomography device to perform:

an analysis processing instruction of sequentially displaying the motion contrast data on a display unit to display real-time three-dimensional motion contrast data on the display unit.

(12) The optical coherence tomography device according to (8), wherein the OCT signal acquiring instruction scans, with measurement light at a plurality of different crossing positions of the test substance so as to acquire the OCT signal for acquiring three-dimensional motion contrast data regarding XY directions, wherein the calculation instruction processes OCT signals at the plurality of crossing positions so as to acquire the three-dimensional motion contrast data, and wherein the computer program, when executed by the processor, further causes the optical coherence tomography device to perform:

an analysis processing instruction of sequentially acquiring the three-dimensional motion contrast data, sequentially acquiring OCT functional enface image data which is enface image data in a predetermined depth region of the test substance based on the three-dimensional motion contrast data, and sequentially displaying the OCT functional enface image data at each crossing position on a display unit to display real-time OCT functional enface image data on the display unit.

(13) The optical coherence tomography device according to (1), wherein the calculation processing instruction processes the plurality of acquired OCT signals so as to acquire motion contrast data of a subject's eye, and wherein the computer program, when executed by the processor, further causes the optical coherence tomography device to perform:

an analysis processing instruction of processing the acquired motion contrast data so as to acquire position information of a blood vessel, and acquiring analysis information regarding the blood vessel based on the position information.

(14) The optical coherence tomography device according to (13), wherein the analysis processing instruction processes the motion contrast data as the analysis information so as to determine whether or not the blood vessel is present, and acquires the analysis information based on a determination result.

(15) The optical coherence tomography device according to (14), wherein the analysis processing instruction processes the motion contrast data so as to determine whether or not the blood vessel is present in a region in a depth direction of the motion contrast data, and acquires analysis information based on a determination result.

(16) The optical coherence tomography device according to (13), wherein the OCT signal acquiring instruction scans, with measurement light, a plurality of different crossing positions on the subject's eye so as to acquire the OCT signal for acquiring three-dimensional functional OCT image data regarding XY directions, wherein the calculation processing instruction processes the plurality of OCT signals acquired at the plurality of crossing positions on the subject's eye so as to acquire the three-dimensional functional OCT image data as the motion contrast data of the subject's eye, and wherein the analysis processing instruction processes the three-dimensional functional OCT image data so as to acquire analysis information regarding a blood vessel for each position on the subject's eye as the analysis information, acquires OCT functional enface image data which is the enface image data in a predetermined depth region of the test substance based on the three-dimensional functional OCT image data, and outputs the OCT functional enface image data and the analysis information in such a manner that the OCT functional enface image data can be compared with the analysis information.

(17) The optical coherence tomography device according to (13), wherein the OCT signal acquiring instruction scans, with measurement light, a plurality of different crossing positions on the subject's eye so as to acquire an OCT signal for acquiring three-dimensional functional OCT image data regarding XY directions, wherein the calculation processing instruction processes the plurality of OCT signals acquired at the plurality of crossing positions on the subject's eye so as to acquire the three-dimensional functional OCT image data as the motion contrast data of the subject's eye, and wherein the analysis processing instruction processes the three-dimensional functional OCT image data so as to acquire analysis information regarding a blood vessel for each position on the subject's eye as the analysis information, and displays the three-dimensional functional OCT image data and the analysis information in such a manner that the three-dimensional functional OCT image data can be compared with the analysis information.

(18) The optical coherence tomography device according to (16), wherein the analysis processing instruction divides the three-dimensional functional OCT image data into a plurality of regions so as to determine whether or not the blood vessel is present in each divided region for each divided region, and acquires analysis information based on a determination result.

(19) An optical coherence tomography calculation method comprising:

acquiring enface image data of a test substance;

acquiring a plurality of OCT signals which are temporally different from each other with respect to the same position on a test substance, at the plurality of positions on the test substance;

processing the plurality of acquired OCT signals so as to acquire three-dimensional functional OCT image data of the test substance;

processing at least one of the acquired OCT signal at each of the plurality of positions so as to acquire reference enface image data of the test substance;

detecting a positional deviation between the enface image data and the reference enface image data; and correlating the enface image data with the three-dimensional functional OCT image data based on the positional deviation.

(20) A non-transitory computer readable recording medium storing an optical coherence tomography calculation program executed in a control device which controls an operation of an optical coherence tomography device, the program being executed by a processor of the control device so as to cause the optical coherence tomography device to perform:

an enface image data acquiring instruction of acquiring enface image data of a test substance;

a OCT signal acquiring instruction of acquiring a plurality of OCT signals which are temporally different from each other with respect to the same position on a test substance, at the plurality of positions on the test substance;

a calculation instruction of processing the plurality of acquired OCT signals so as to acquire three-dimensional functional OCT image data of the test substance, and processing at least one of the acquired OCT signal at each of the plurality of positions so as to acquire reference enface image data of the test substance;

a detecting instruction of detecting a positional deviation between the enface image data and the reference enface image data; and a correlating instruction of correlating the enface image data with the three-dimensional functional OCT image data based on the positional deviation.

DESCRIPTION OF ILLUSTRATIVE EMBODIMENTS

A preferred embodiment of the present invention will be described with reference to the drawings. In addition, in the present embodiment, a depth direction (an axial direction of an subject's eye E) of a subject's eye is set to a Z direction (a direction of an optical axis L1), a horizontal direction on a plane (the same plane as a face of a subject) perpendicular to the depth direction is set to an X direction, and a vertical direction is set to a Y direction. Surface directions of the fundus may be considered as XY directions.

Figure 1:
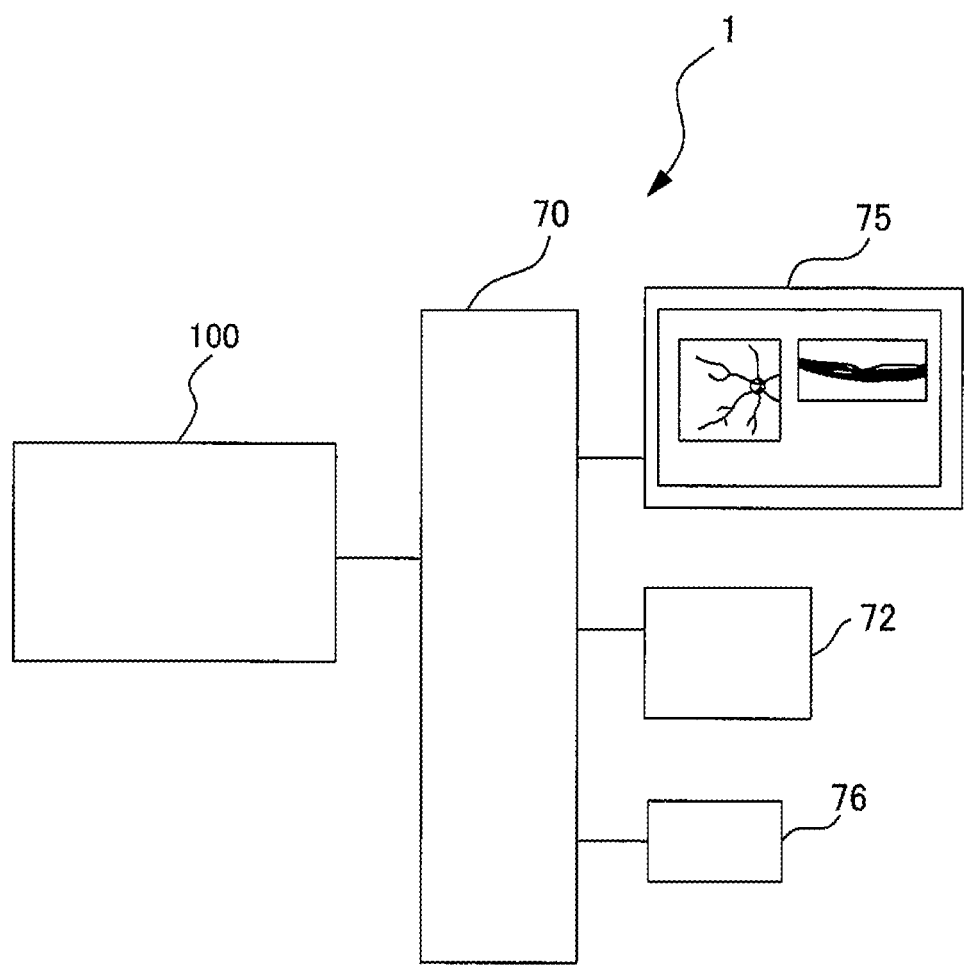
FIG. 1 is a block diagram illustrating a configuration of an optical coherence tomography device according to the present example.

The present device (optical coherence tomography device) 1 mainly includes an interference optical system (OCT optical system) 100, a fundus illumination optical system (hereinafter, simply referred to as an illumination optical system in some cases) 10, a CPU (control unit) 70, a monitor 75, an operation unit 76, and a memory 72 (refer to FIG. 1). The respective units are electrically connected to the control unit 70 via a bus or the like. In the following description, as an example, a description will be made of a case where the optical coherence tomography device 1 captures a tomographic image of the fundus Ef of the subject's eye E. Of course, the optical coherence tomography device 1 is applicable to imaging of various sites (for example, the anterior chamber) of the subject's eye.

As an example of the optical coherence tomography device 1, a device in which the OCT optical system 100 is integrally formed with the various units has been described but is not limited thereto. For example, the OCT device 1 may be configured not to include the OCT optical system 100. In this case, the OCT device is connected to another device including the OCT optical system which is provided separately, receives an OCT signal or OCT image data which is acquired by another device, and performs various calculation processes based on the received information.

For example, the control unit 70 controls an operation of each unit based on a calculation program, various control programs, and the like stored in the memory 72 (details thereof will be described later). In addition, by using a calculation processing unit, an input unit, a storage unit, and a display unit included in a personal computer (PC) which is available commercially as the control unit 70, the operation unit 76, the memory 72, and the monitor 75, various programs may be installed in the PC which is available in the market. For example, the control unit 70 may also be used as acquisition means, calculation processing means, analysis processing means, image processing means, and the like. Further, the control unit 70 may also be used as control means (scanning control means) for controlling scanning means for performing scanning with measurement light. Of course, the acquisition means, the calculation processing means, the analysis processing means, the image processing means, the scanning control means, and the like may be provided separately.

For example, the OCT optical system 100 irradiates the fundus Ef with measurement light. The OCT optical system 100 detects an interference state between the measurement light reflected from the fundus Ef and reference light by using a light receiving element (a detector 120). The OCT optical system 100 includes irradiation position changing units (for example, an optical scanner 108 and a fixation target projection unit 300) which changes an irradiation position of measurement light on the fundus Ef in order to change an imaging position on the fundus Ef. The control unit 70 controls operations of the irradiation position changing units based on set imaging position information, and acquires tomographic image data based on a light reception signal from the detector 120. The tomographic image data may be image data, and may be signal data.

As the tomographic image data, there may be, for example, B scan tomographic image data and three-dimensional tomographic image data (three-dimensional OCT image data). For example, the B scan tomographic image data is tomographic image data acquired by performing scanning with measurement light in one direction (for example, the X direction) of the XY directions along a scanning line (crossing position). In addition, for example, the three-dimensional OCT image data is tomographic image data acquired by performing scanning with measurement light in a two-dimensional manner. For example, an OCT enface image (for example, an integrated image obtained through integration in a depth direction, an integrated value of spectral data at respective XY positions, luminance data at respective XY positions in a specific depth direction, or a superficial capillary image) may be acquired based on the three-dimensional OCT image data.

For example, the OCT optical system 100 includes an enface observation optical system 200. Of course, the enface observation optical system 200 may be separately provided.

In this case, a device including the enface observation optical system 200 is connected to the optical coherence tomography device 1, the OCT optical system 100, or the like, receives enface image data acquired by the device including the enface observation optical system 200 which is separately provided, and performs various calculation processes based on the received information.

For example, the enface observation optical system 200 acquires enface image data of a subject's eye. The enface image data may be image data, and may be signal data. For example, the enface observation optical system 200 is provided to obtain an enface image of the fundus Ef. As the enface observation optical system 200, for example, a scanning laser ophthalmoscope (SLO), or a fundus camera type configuration may be used. For example, the OCT optical system 100 may also be used as the enface observation optical system 200. In other words, enface image data (hereinafter, referred to as an enface image) may be acquired by using data forming a tomographic image (an OCT enface image) which is obtained in a two-dimensional manner.

For example, the control unit 70 acquires a plurality of OCT signals which are temporally different from each other with respect to the same position on a test substance (for example, a subject's eye). The control unit 70 processes the plurality of acquired OCT signals so as to acquire motion contrast data in the test substance. Incidentally, the plurality of OCT signals which are temporally different from each other with respect to the same position on the test substance may be the plurality of OCT signals which are generated by the OCT optical system which captures images of the same position on the test substance at different timings.

For example, the motion contrast data is detection information regarding a motion, a temporal change, or the like of the test substance. For example, a flow image is a kind of motion contrast. The flow image is obtained by detecting a motion of, for example, a fluid, and generating the detected motion as an image. For example, angiographic image data or the like in which a blood vessel position obtained by detecting a motion of blood is imaged can be said to be a kind of motion contrast data.

Examples of the motion contrast data may include a functional OCT signal, functional OCT image data, and three-dimensional functional OCT image data (three-dimensional motion contrast data). In other words, the motion contrast data may be image data, and may be signal data. For example, the functional OCT signal is so-called A scan data. In addition, for example, the functional OCT image data is acquired by arranging the functional OCT signals at respective scanning positions of measurement light. Further, for example, the three-dimensional functional OCT image data is acquired by performing scanning with measurement light in the XY directions in a two-dimensional manner. Still further, OCT functional enface image data (for example, an integrated image obtained through integration in a depth direction, an integrated value of spectral data at respective XY positions, or luminance data at respective XY positions in a specific depth direction) or the like may be acquired from the three-dimensional functional OCT image data.

For example, the control unit 70 scans the same position on a test substance with measurement light at least twice, and acquires temporally different OCT signals at the same position. As the temporally different OCT signals at the same position, signals at the same position are preferably acquired. In addition, a plurality of temporally different OCT signals may not be signals which are obtained by scanning exactly the same position with measurement light. For example, positions adjacent to each other may be scanned. As mentioned above, the same position includes scanning positions adjacent to each other.

<Calculation Processing Operation>

For example, the control unit 70 acquires a plurality of OCT signals at a first position on a test substance, and then acquires a plurality of OCT signals at a second position which is different from the first position. The control unit 70 processes the plurality of OCT signals acquired at the first position during the acquisition of the plurality of OCT signals at either or both of the first position and the second position, and acquires motion contrast data at the first position. With this configuration, since the OCT signals can be processed and the processing of the OCT signals can be completed during the acquisition of the plurality of OCT signals, the motion contrast data can be rapidly acquired.

Examples of the calculation processing method for acquiring motion contrast data may include a method using a phase difference (PD) of complex OCT signals, a method using a vector difference (VD) of complex OCT signals, and a method using a speckle variance (SV). For example, the calculation processing method may employ combinations of the methods.

For example, in a case where at least two OCT signals are acquired at the first position, the control unit 70 may start processing of the OCT signals acquired at the first position even if OCT signals are continuously acquired at the first position. In addition, for example, if acquisition of a plurality of OCT signals at the second position is started, the control unit 70 may start processing of the plurality of OCT signals at the first position. In addition, for example, processing of a plurality of OCT signals at the first position may be started at a timing at which acquisition of OCT signals at a position (for example, a third position) which is different from the first position is started. Further, processing of a plurality of OCT signals at the first position is started at a timing at which acquisition of OCT signals at a different position (for example, the second position or the third position) is started, but, strictly, processing of OCT signals may not be started at a timing at which acquisition of OCT signals at a different position is started. In other words, processing of OCT signals at the first position may be started at any timing at which acquisition of OCT signals at a different position is in progress.

Each of the first position and the second position may be, for example, a single position (A scan line) or a single crossing position. For example, in a case where the first position is a first crossing position, and the second position is a second crossing position, the control unit 70 processes a plurality of OCT signals detected at the first crossing position and acquires motion contrast data at the first crossing position during acquisition of a plurality of OCT signals at either of both of the first crossing position and the second crossing position. As mentioned above, in a case where a plurality of OCT signals are acquired in the units of the crossing positions, the OCT signals are processed, and thus the processing can be performed by taking into consideration deviations in a crossing direction and a depth direction. Therefore, it is possible to acquire more favorable motion contrast data.

For example, the control unit 70 may acquire motion contrast data at the respective positions and may also display the motion contrast data on the monitor 75. With this configuration, it is possible to check whether or not motion contrast data is acquired with high accuracy at a position where acquisition of an OCT signal has been completed before acquisition of OCT signals at all set imaging positions is completed. For this reason, it is possible to reduce unnecessary re-imaging after imaging is completed.

<Process of Correlation with Three-Dimensional Functional OCT Image Data>

For example, the control unit 70 aligns three-dimensional functional OCT image data with other enface image data. For example, the three-dimensional functional OCT image data is acquired by processing a plurality of OCT signals which are acquired at a plurality of positions on a test substance, and the control unit 70 processes at least one OCT signal at each of the plurality of positions among the plurality of OCT signals acquired at the plurality of positions on the test substance, and acquires reference enface image data of the test substance. The control unit 70 matches other enface image data with the reference enface image data so as to correlate other enface image data with the three-dimensional functional OCT image data. In the above-described way, since the three-dimensional functional OCT image data and the enface image data (reference enface image data) for alignment can be acquired by using a common OCT signal, even if there is a difference in the type of image data (for example, a luminance distribution, contrast, a resolution, and a form of a test substance) from other enface image data which is correlated with the three-dimensional functional OCT image data, the correlation can be easily performed with high accuracy. In addition, if three-dimensional functional OCT image data used for an angiographic image is correlated with other fundus image data so as to be used as an angiographic image, a relationship of both of the data items can be easily identified, and thus information useful for diagnosis can be acquired.

For example, as the three-dimensional functional OCT image data, not only the three-dimensional functional OCT image data but also OCT functional enface image data acquired from the three-dimensional functional OCT image data may be used.

For example, as other enface image data, enface image data acquired by the enface observation optical system (for example, an SLO or a fundus camera type configuration) 200 may be used. Of course, enface image data which is separately acquired by another device may be used.

For example, as reference enface image data, OCT enface image data may be used which is acquired based on at least one OCT signal of a plurality of OCT signals acquired at a plurality of positions on the test substance. In addition, for example, as the reference enface image data, OCT functional enface image data acquired based on three-dimensional functional OCT image data may be used.

For example, the control unit 70 correlates enface image data and three-dimensional functional OCT image data with each other so as to superimpose display indicating the three-dimensional functional OCT image data on the enface image data. As mentioned above, since the enface image data and the display indicating the three-dimensional functional OCT image data are superimposed on each other through the correlation, a relationship between both of the data items can be easily identified, and thus information useful for diagnosis can be obtained. For example, in a case where OCT functional enface image data is used as three-dimensional functional OCT image data, the control unit 70 acquires OCT functional enface image data which is enface image data in a predetermined depth region of the test substance based on the three-dimensional functional OCT image data. The control unit 70 correlates the enface image data with the three-dimensional functional OCT image data so as to superimpose display indicating the OCT functional enface image data on the enface image data. Of course, the enface image data, the three-dimensional functional OCT image data, and the OCT functional enface image data are displayed in a superimposed manner.

<Analysis Information Acquisition Process>

For example, the control unit 70 may acquire analysis information regarding a blood vessel based on motion contrast data. For example, the control unit 70 processes motion contrast data for a subject's eye so as to acquire position information of a blood vessel, and acquires analysis information regarding the blood vessel based on the position information. As mentioned above, if the analysis information regarding the blood vessel is acquired, a retinal disease can be detected early. In addition, it is possible to check a blood vessel activity state with the simple configuration and thus to confirm an effect of a drug, laser treatment, or the like.

For example, in relation to analysis information, the control unit 70 may process motion contrast data so as to determine whether or not a blood vessel is present and may acquire the analysis information based on a determination result. With this configuration, lesions or the like which can be determined based on the presence or absence of a blood vessel can be easily found early. In addition, for example, in relation to analysis information, the control unit 70 measures at least one of a dimension (length information), an area, and a volume (a volume, a volume ratio, or the like which is actually calculated) through image processing, and may acquire a blood vessel analysis parameter (analysis parameter) based on a measurement result.

For example, in a case where it is determined whether or not a blood vessel is present by processing motion contrast data, the control unit 70 determines whether or not a blood vessel is present in a region in the depth direction of the motion contrast data and acquires analysis information based on a determination result. With this configuration, it is possible to identify the presence or absence of a blood vessel in the depth direction at each position of the subject's eye and thus to easily find lesions or the like early. For example, the region in the depth direction of the motion contrast data may be all regions in the depth direction. For example, the region in the depth direction of the motion contrast data may be some regions in the depth direction of the motion contrast data. If a determination is performed based on such some regions, a blood vessel state in a predetermined depth can be checked, and thus more specific blood vessel analysis information can be provided to an examiner.

EXAMPLE

Figure 2:
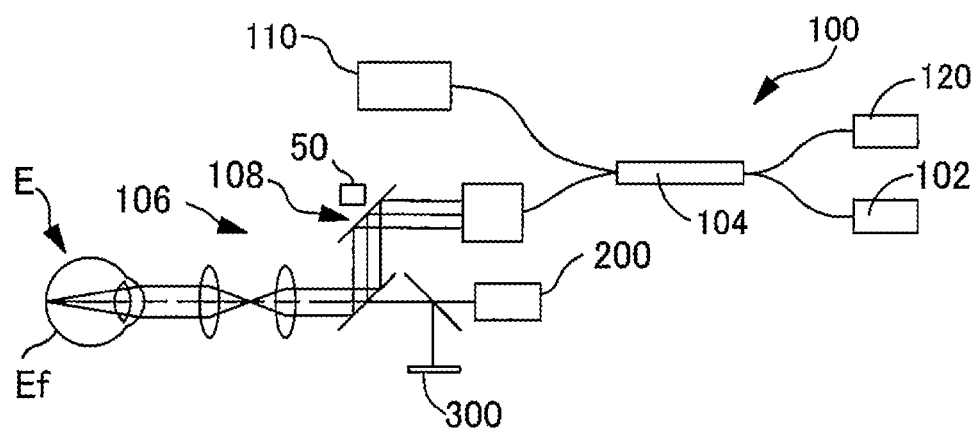
FIG. 2 is a diagram illustrating a schematic OCT optical system according to the present example.

Hereinafter, one preferred example will be described with reference to the drawings. FIG. 1 is a block diagram illustrating a configuration of an optical coherence tomography device related to the present example. FIG. 2 is a schematic diagram illustrating an OCT optical system.

The optical coherence tomography device (hereinafter, referred to as an OCT device) 1 processes a detection signal acquired by the OCT optical system (interference optical system) 100. In the present example, the OCT device 1 displays a fundus image captured by the OCT optical system 100 on display means (for example, a monitor) 75 for observation. For example, the OCT device 1 is constituted of the OCT optical system, the CPU (control unit) 70, the mouse (operation unit) 76, the memory (storage unit) 72, and the monitor 75, and the respective units are electrically connected to the CPU 70 via a bus. In addition, in the following description, as an example, a description will be made of a case where the OCT device 1 captures a tomographic image of the fundus Ef of the subject's eye E.

The control unit 70 controls an operation of each unit based on a calculation program, various control programs, and the like stored in the memory 72 (details thereof will be described later). In addition, by using a calculation processing unit, an input unit, a storage unit, and a display unit included in a personal computer (PC) which is available in the market as the control unit 70, the operation unit 76, the memory 72, and the monitor 75, various programs may be installed in the PC which is available in the market.

In addition, in the present example, as an example of the OCT device 1, a device in which the OCT optical system 100 is integrally formed with the various units has been described but is not limited thereto. For example, the OCT device 1 may be configured not to include the OCT optical system 100. In this case, the OCT device is connected to another device including the OCT optical system which is provided separately, receives an OCT signal or OCT image data, and performs various calculation processes based on the received information.

For example, in the present example, the OCT optical system 100 includes the enface observation optical system 200. Of course, the OCT optical system may not be integrally formed with the enface observation optical system 200. The OCT optical system 100 irradiates the fundus Ef with measurement light. The OCT optical system 100 detects an interference state between the measurement light reflected from the fundus Ef and reference light by using a light receiving element (a detector 120). The OCT optical system 100 includes irradiation position changing units (for example, an optical scanner 108 and a fixation target projection unit 300) which changes an irradiation position of measurement light on the fundus Ef in order to change an imaging position on the fundus Ef. The control unit 70 controls operations of the irradiation position changing units based on set imaging position information, and acquires tomographic image data based on a light reception signal from the detector 120.

<OCT Optical System>

The OCT optical system 100 will be described. The OCT optical system 100 has a optical coherence tomography (OCT) configuration and captures a tomographic image of the subject's eye E. The OCT optical system 100 splits light emitted from a measurement light source 102 into measurement light (sample light) and reference light by using a coupler (beam splitter) 104. In addition, the OCT optical system 100 guides the measurement light to the fundus Ef of the eye E by using a measurement optical system 106 and guides the reference light to a reference optical system 110. Then, interference light obtained by combining the measurement light reflected from the fundus Ef and the reference light is received by the detector 120.

The detector 120 detects an interference signal between the measurement light and the reference light. In a case of a Fourier-domain OCT, a spectral intensity (spectral interference signal) of the interference light is detected by the detector 120, and a complex OCT signal is acquired through Fourier transform on the spectral intensity data.

For example, in the Fourier-domain OCT, a depth profile (A scan signal) within a predetermined range is acquired by calculating an absolute value of the amplitude of a complex OCT signal which is acquired through Fourier transform on spectral intensity data. OCT image data (tomographic image data) is acquired by arranging depth profiles at respective scanning positions of measurement light emitted from the optical scanner 108. In addition, scanning may be performed with the measurement light in a two-dimensional manner, and thus three-dimensional OCT image data (three-dimensional tomographic image data) may be acquired. Further, an OCT enface image (for example, an integrated image obtained through integration in a depth direction, an integrated value of spectral data at respective XY positions, luminance data at respective XY positions in a specific depth direction, or a superficial capillary image) may be acquired from the three-dimensional OCT image data.

Still further, motion contrast data is acquired based on two or more OCT signals which are temporally different from each other at the same position. In other words, at least two complex OCT signals are analyzed, and thus the motion contrast data is acquired. For example, a functional OCT signal is acquired by using the complex OCT signal. The functional OCT signals at respective scanning positions of measurement light emitted from the optical scanner 108 are arranged, and thus functional OCT image data is acquired. Furthermore, scanning is performed with the measurement light in a two-dimensional manner in the XY directions, and thus three-dimensional functional OCT image data (three-dimensional motion contrast data) is acquired. Moreover, an OCT functional enface image (for example, a doppler enface image or a signal image speckle variation enface image) is acquired based on the three-dimensional functional OCT image data. In addition, each image data item may be image data, and may be signal data. Details of the motion contrast data will be described later.

Examples of the Fourier-domain OCT may include spectral-domain OCT (SD-OCT) and swept source OCT (SS-OCT). For example, time-domain OCT (TD-OCT) may be used. In a case of the SD-OCT, a low coherent light source (a wide area light source) is used as the light source 102, and the detector 120 is provided with a spectral optical system (spectrometer) which separates interference light into respective frequency components (respective wavelength components). The spectrometer is constituted of, for example, a diffraction grating and a line sensor. In a case of the SS-OCT, a wavelength scanning type light source (wavelength variable light source) which changes emitted wavelengths temporally at a high speed is used as the light source 102, and a single light receiving element is provided as the detector 120. The light source 102 is constituted of, for example, a light source, a fiber ring resonator, and a wavelength selection filter. As the wavelength selection filter, for example, a combination of a diffraction grating and a polygon mirror, or one using Fabry-Perot etalon may be used.

Light emitted from the light source 102 is split into measurement light beams and reference light beams by the coupler 104. The measurement light beams pass through an optical fiber and are emitted to air. The light beams are collected at the fundus Ef via the optical scanner 108 and other optical members of the measurement optical system 106. Light reflected from the fundus Ef is returned to the optical fiber along the same optical path.

The optical scanner 108 scans the fundus with measurement light in a two-dimensional manner (XY directions). The optical scanner 108 is disposed at a position substantially conjugate to the pupil. The optical scanner 108 is constituted of, for example, two galvano mirrors, and reflection angles thereof are arbitrarily adjusted by a driving mechanism 50.

Consequently, reflection (traveling) directions of light beams emitted from the light source 102 are changed, and the fundus is scanned with the light beams at any position. Thus, an imaging position on the fundus Ef is changed. The optical scanner 108 may have a configuration of deflecting light. For example, not only a reflective mirror (a galvano mirror, a polygon mirror, or a resonant scanner) but also an acousto-optical element (AOM) which changes a traveling (deflection) direction of light is used.

The reference optical system 110 generates reference light which is combined with reflected light obtained by reflection of measurement light on the fundus Ef. The reference optical system 110 may be of a Michelson type, and may be of a Mach-Zenhder type. The reference optical system 110 is constituted of, for example, a reflection optical system (for example, a reference mirror), and reflects light from the coupler 104 with the reflection optical system so that the light is returned to the coupler 104 and is thus guided to the detector 120. As another example, the reference optical system 110 is constituted of a transmission optical system (for example, an optical fiber), and transmits light from the coupler 104 through the transmission optical system without returning the light so that the light is guided to the detector 120.

The reference optical system 110 has a configuration of changing an optical path length difference between measurement light and reference light by moving an optical member on a reference optical path. For example, the reference mirror is moved in an optical axis direction. The configuration of changing an optical path length difference may be disposed on a measurement optical path of the measurement optical system 106.

<Enface Observation Optical System>

The enface observation optical system 200 acquires enface image data of the subject's eye. In addition, the enface image data may be image data, and may be signal data. For example, the enface observation optical system 200 is provided to obtain an enface image of the fundus Ef. The enface observation optical system 200 includes, for example, an optical scanner which scans the fundus with measurement light (infrared light) emitted from a light source in a two-dimensional manner, and a second light receiving element which receives light reflected from the fundus via a confocal aperture which is disposed at a position substantially conjugate to the fundus, and has a scanning laser ophthalmoscope (SLO) configuration.

In addition, a configuration of the enface observation optical system 200 may be a so-called fundus camera type configuration. Further, the OCT optical system 100 may also be used as the enface observation optical system 200. In other words, enface image data (hereinafter, referred to as an enface image) may be acquired by using data forming a tomographic image (OCT enface image) which is two-dimensionally obtained.

The enface observation optical system 200 may not be integrally formed with the OCT device or the like. In this case, enface image data acquired by the enface observation optical system 200 which is separately provided is received by the OCT device or the like.

<Fixation Target Projection Unit>

The fixation target projection unit 300 includes an optical system for guiding a visual line direction of the eye E. The fixation target projection unit 300 has a fixation target presented to the eye E, and can guide the eye E in a plurality of directions.

For example, the fixation target projection unit 300 includes a visible light source which emits visible light, and two-dimensionally changes a target presentation position. Consequently, a visual line direction is changed, and thus an imaging part is changed. For example, if a fixation target is presented from the same direction as an imaging optical axis, a central part of the fundus is set as an imaging part. In addition, if a fixation target is presented upward with respect to the imaging optical axis, an upper part of the fundus is set as an imaging part. In other words, an imaging part is changed depending on a position of the target relative to the imaging optical axis.

The fixation target projection unit 300 may have various configurations such as a configuration in which a target position is adjusted depending on turned-on positions of LEDs which are arranged in a matrix, and a configuration in which an optical scanner performs scanning with light from a light source, and a target position is adjusted by controlling turning-on of the light source. The fixation target projection unit 300 may be of an internal target type, and may be of an external target type.

<Control Unit>

The control unit 70 includes a CPU (processor), a RAM, a RAM, and the like. The CPU of the control unit 70 controls the entire device such as the respective members of the constituent elements 100 to 300. The RAM temporarily stores various pieces of information. The ROM of the control unit 70 stores various programs, initial values, and the like for controlling an operation of the entire device. The control unit 70 may be constituted of a plurality of control units (that is, a plurality of processors).

The control unit 70 is electrically connected to the non-volatile memory (storage means) 72, the operation unit 76, the display unit (monitor) 75, and the like. The nonvolatile memory (memory) 72 is a non-transitory storage medium which can hold storage content even if power is not supplied. For example, a hard disk drive, a flash ROM, and a USB memory which is attachable to and detachable from the OCT device 1 and the OCT optical system 100 may be used as the nonvolatile memory 72. The memory 72 stores an imaging control program for controlling the OCT optical system 100 to capture an enface image and a tomographic image. In addition, the memory 72 stores a fundus analysis program which enables the OCT device 1 to be used. Further, the memory 72 stores various information pieces regarding imaging, such as information regarding imaging positions on a scanning line for tomographic image data (OCT image data), three-dimensional tomographic image data (three-dimensional OCT image data), enface image data (fundus enface image data), and tomographic image data. An examiner inputs various operation instructions to the operation unit 76.

The operation unit 76 outputs a signal corresponding to an input operation instruction to the control unit 70. The operation unit 76 may employ at least one of, for example, a mouse, a joystick, a keyboard, and a touch panel.

The monitor 75 may be a display mounted in the device main body, and may be a display connected to the main body. A display of a personal computer ("PC") may be used. A plurality of displays may be used. The monitor 75 may be a touch panel. If the monitor 75 is a touch panel, the monitor 75 functions as an operation unit. Various images including tomographic image data and enface image data captured by the OCT optical system 100 are displayed on the monitor 75.

<Signal Processing Method>

In a calculation processing method for acquiring motion contrast data based on an OCT signal in the present example, the control unit 70 acquires interference signals (OCT signals) of at least two frames which are temporally different from each other at the same position in order to acquire the motion contrast data.

In the present example, the control unit 70 performs a process using a doppler phase difference method and a process using a vector difference method and acquires motion contrast data (for example, functional OCT image data) based on a plurality of OCT signals. As a method of processing a complex OCT signal, there may be, for example, a method of calculating a phase difference between complex OCT signals, a method of calculating a vector difference between complex OCT signals, and a method of multiplying a phase difference and a vector difference between complex OCT signals together. In the present example, the method of multiplying a phase difference and a vector difference together will be described as an example.

Next, the control unit 70 performs Fourier transform on an OCT signal acquired by the OCT optical system. The control unit 70 obtains a complex OCT signal through the Fourier transform. The complex OCT signal includes a real number component and an imaginary number component.

In order to obtain a blood flow signal, it is necessary to compare images which are temporarily different from each other at the same position, with each other. For this reason, the control unit 70 preferably performs alignment of images based on image information. Image registration is a process of arranging and disposing a plurality of images of the same scene. As a cause of a position of the image being deviated, there may be, for example, a movement (for example, fixational eye movement, microfluctuation of accommodation, or pulsation) of a subject's eye during imaging. In addition, even if the frames are aligned, a phase deviation between A scan lines in the same image may occur. Therefore, phase correction is preferably performed. Further, the registration and the phase correction process are performed in order to facilitate a process of the present example and are not essential.

Next, the control unit 70 calculates a phase difference between at least two complex OCT signals which are temporally different from each other at the same position. The control unit 70 removes a random phase difference which is present in a region where a signal to noise ratio (S/N ratio) is low.

The control unit 70 removes a portion having a small phase difference. This is aimed at removing a reflected signal from a highly reflective portion such as a nerve fiber layer (NFL). Consequently, it is easy to differentiate a signal from a highly reflective portion from a signal from a blood vessel. In the present example, a single frame for calculating a phase difference is acquired. In addition, in a case where there are process frames for calculating a phase difference, more preferably, the control unit 70 adds and averages signals of frames on which the above-described process has been performed, so as to remove noise.

Next, the control unit 70 calculates a vector difference between complex OCT signals. For example, a vector difference between complex OCT signals detected by the OCT optical system is calculated. For example, the complex OCT signal may be represented as a vector on a complex plane. Therefore, two signals which are temporally different from each other at the same position are detected for calculation of a vector difference, and thus angiographic image data of a subject's eye is generated. In a case where the vector difference is generated as an image, for example, an image may be generated based on not only a size of a difference but also phase information. In the present example, a single frame for calculating a vector difference is acquired. In addition, in a case where there are process frames for calculating a vector difference, more preferably, the control unit 70 adds and averages signals of frames on which the above-described process has been performed, so as to remove noise.

The control unit 70 uses a phase difference calculation result in a vector difference calculation result as a filter. In addition, in description of the present example, "applying a filter" indicates, for example, that weighting is performed on a certain numerical value. For example, the control unit 70 performs weighting by applying a phase difference calculation result to a vector difference calculation result. In other words, a vector difference of a portion with a small phase difference is weakened, and a vector difference of a portion with a large phase difference is strengthened. Consequently, the vector difference calculation result is weighted by the phase difference calculation result.

In the process according to the present example, the control unit 70, for example, multiplies a vector difference calculation result and a phase difference calculation result together. Consequently, the control unit 70 generates functional OCT image data weighted by the phase difference calculation result.

By multiplying a vector difference calculation result and a phase difference calculation result together, deficiencies of each measurement method can be removed, and thus image data of a blood vessel portion can be skillfully acquired.

The control unit 70 performs the calculation process for each scanning line and acquires functional OCT image data for each scanning line. In addition, the functional OCT image data is acquired at a plurality of positions, and thus three-dimensional functional OCT image data which is used as a pseudo-angiographic image can be acquired.

In the present example, a description has been made of an example of a configuration in which the control unit 70 multiplies a vector difference calculation result and a phase difference calculation result together in order to acquire motion contrast data, but the present example is not limited thereto. For example, motion contrast data may be acquired by using a vector difference calculation result. In addition, for example, motion contrast data may be acquired by using a phase difference calculation result.

In the present example, a description has been made of an example of a configuration in which the control unit 70 acquires motion contrast data by using two OCT signals, but the present example is not limited thereto. Motion contrast data may be acquired by using two or more OCT signals.

<Imaging Operation>

Hereinafter, a series of imaging operations using the OCT device 1 will be described. In the following description, a case of acquiring three-dimensional functional OCT image data will be described as an example. Of course, a technique disclosed in the present invention is applicable to acquisition of motion contrast data. For example, the technique is applicable to a case where a functional OCT signal is acquired or a case where functional OCT image data is acquired.

First, an examiner instructs a subject to gaze at a fixation target of the fixation target projection unit 300, and then performs an alignment operation by using the operation unit 76 (for example, a joystick (not illustrated)) so that a measurement optical axis comes to the pupil center of the subject's eye while observing an anterior chamber observation image captured by an anterior chamber observation camera (not illustrated) on the monitor 75.

For example, if the alignment operation is completed, the control unit 70 controls the OCT optical system 100 to acquire three-dimensional OCT image data corresponding to a set region and also controls the enface observation optical system 200 to acquire fundus image data (fundus enface image data). In addition, the control unit 70 acquires three-dimensional OCT image data by using the OCT optical system 100 and acquires fundus image data by using the enface observation optical system 200 at any time. The three-dimensional OCT image data includes image data in which A scan signals are arranged in the XY directions in a two-dimensional manner, a three-dimensional graphic image, and the like.

The examiner sets a scanning position by using a fundus enface image from the enface observation optical system 200. If an imaging start signal is output from the operation unit 76, the control unit 70 controls an operation of the optical scanner 108 to perform scanning with measurement light in the XY directions in a two-dimensional manner within a scanning range corresponding to an imaging region and thus starts acquisition of three-dimensional functional OCT image data. As a scanning pattern, for example, a raster screen, and a plurality of line scan may be used.

Figure 3:
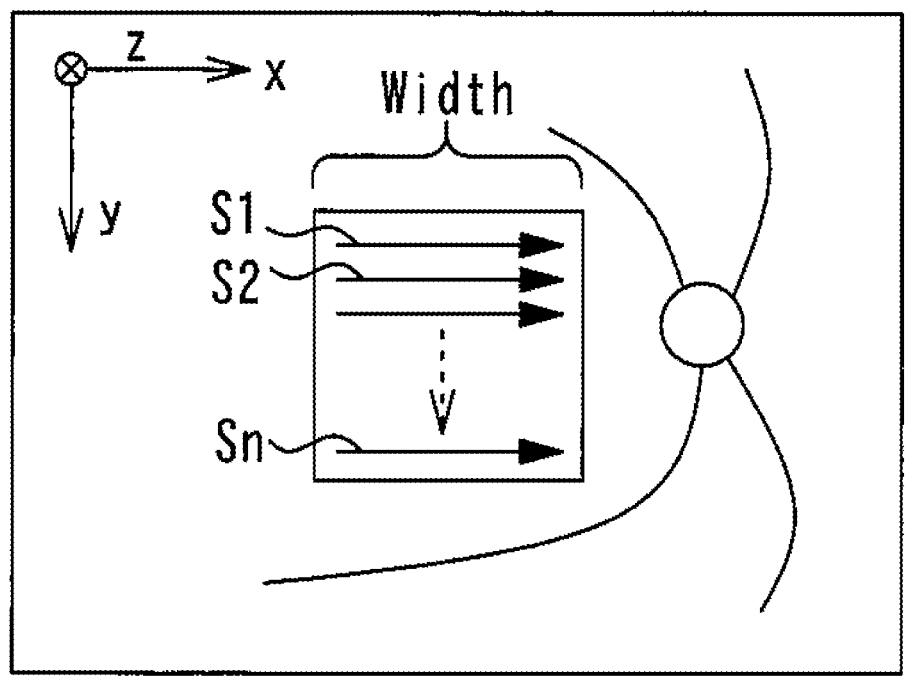
FIG. 3 is a diagram of the fundus for explaining imaging in the present example.

Hereinafter, a description will be made of an imaging operation using the OCT device 1. FIG. 3 is a schematic diagram for explaining imaging in the present example.

For example, if an imaging start signal is output, the control unit 70 controls driving of the optical scanner 108 to scan the fundus with measurement light in order to acquire three-dimensional functional OCT image data. For example, scanning is performed with measurement light in the X direction along a first scanning line (crossing position) S1 illustrated in FIG. 3. As mentioned above, scanning with measurement light in one (for example, the X direction) of the XY directions is referred to as a "B scan". Hereinafter, an interference signal of one frame is referred to as an OCT signal obtained through one B scan. The control unit 70 acquires an OCT signal detected by the detector 120 during the scanning. In FIG. 3, a Z axis direction is set as an optical axis direction of the measurement light. An X axis direction is set as a direction perpendicular to the Z axis and is a horizontal direction. A Y axis direction is set as a direction perpendicular to the Z axis and is a vertical direction.

If the first scanning is completed, the control unit 70 performs second scanning at the same position as in the first scanning. For example, the control unit 70 performs scanning with measurement light along the first scanning line S1 illustrated in FIG. 3 and then performs scanning with the measurement light again. The control unit 70 acquires an OCT signal detected by the detector 120 during the second scanning. Consequently, the control unit 70 can acquire OCT signals of two frames which are temporally different from each other at the same position. The present example has exemplified a configuration in which OCT signals of two frames are acquired at the same position, but is not limited thereto. There may be a configuration in which OCT signals of at least two frames are acquired at the same position. For example, scanning may be repeatedly performed eight times at the same position, and OCT signals of eight consecutive frames which are temporally different from each other may be acquired.

In a case where OCT signals which are temporally different from each other at the same position can be acquired in scanning performed once, second scanning may not be performed. For example, in a case where scanning is performed with two measurement light beams whose optical axes are deviated relative to each other at one time, scanning is not required to be performed plural times as long as OCT signals which are temporally different from each other at the same position in a subject can be acquired. In other words, the same position is not necessarily exactly the same position, and may be substantially the same position. In a case where scanning is performed with two measurement light beams at one time, any blood flow rate can be detected as a target based on an interval of the two measurement light beams.

If the scanning performed multiple times in the first scanning line S1 is completed, the control unit 70 controls the optical scanner 108 to change a sub-scanning position (a position in the Y direction) and to perform scanning multiple times in the main scanning direction (X direction) in a second scanning line S2. The control unit 70 performs the scanning in the second scanning line S2 until OCT signals of a preset number of frames (in the present example, OCT signals of two frames) are obtained.

Similarly, the control unit 70 performs scanning with measurement light plural times in each scanning line up to the last scanning line Sn, so as to acquire a plurality of OCT signals in each scanning line. In other words, the control unit 70 performs scanning plural times in each scanning line. That is, as illustrated in FIG. 3, the control unit 70 performs a raster scan (a scan at the crossing position) with measurement light so as to acquire OCT signals of at least two frames in the respective scanning lines (S1 to Sn). Consequently, it is possible to acquire three-dimensional information regarding the fundus. In addition, the control unit 70 may control the OCT optical system 100 to acquire an OCT signal and may also control the enface observation optical system 200 to acquire fundus image data.

Here, in a case where a calculation process is performed on a plurality of OCT signals acquired in each scanning line, and functional OCT image data is acquired in each scanning line, time to perform the calculation process is taken. For this reason, if a plurality of OCT signals are acquired in each scanning line and then the calculation process on the plurality of OCT signals in each scanning line is started, long time to acquire functional OCT image data in each scanning line is taken.

In the present example, in a case where transfer to acquisition of an OCT signal in the next scanning line is made, an OCT signal in each scanning line, acquired until that time, is processed. The control unit 70 processes a plurality of OCT signals acquired at the first position so as to acquire motion contrast data at the first position during acquisition of a plurality of OCT signals at either or both of the first position and the second position.

For example, the control unit 70 moves an acquisition position of an OCT signal from the first scanning line S1 to the second scanning line S2 after acquiring a plurality of OCT signals in the first scanning line S1. If acquisition of an OCT signal is started in the second scanning line S2, the control unit 70 starts a calculation process on a plurality of OCT signals which have been acquired in the first scanning line S1. In other words, the control unit 70 starts a calculation process on a plurality of OCT signals corresponding to the first scanning line S1 so as to acquire functional OCT image data during acquisition of an OCT signal in the second scanning line S2. The control unit 70 performs the process for each scanning line so as to acquire a plurality of OCT signals in each scanning line and to acquire functional OCT image data in each scanning line. In addition, functional OCT image data is acquired at a plurality of positions (scanning lines), and thus three-dimensional functional OCT image data which is a pseudo-angiographic image (an image which can be used as an angiographic image) can be acquired.

In the present example, an example of a case where the control unit 70 starts a calculation process on a plurality of OCT signals acquired in the first scanning line S1 if acquisition of an OCT signal is started in the second scanning line S2, the present example is not limited thereto. A calibration operation on a plurality of OCT signals may be started during acquisition of a plurality of OCT signals which are different from the OCT signals on which the calibration operation is being performed.

For example, in a case where at least two OCT signals are acquired in the first scanning line S1, the control unit 70 may sequentially perform a calibration operation on OCT signals in the first scanning line S1. In this case, for example, when two OCT signals are acquired in the first scanning line S1, and acquisition of a third OCT signal is started in the first scanning line S1, the control unit 70 starts to process the first OCT signal and the second OCT signal acquired in the first scanning line S1 start to be processed. In addition, for example, the control unit 70 may start a calculation process on a plurality of OCT signals in the first scanning line S1 when starting acquisition of an OCT signal in the third scanning line which is the next position of the second scanning line S2.

As described above, a calculation process on OCT signals at the previous position can be completed during acquisition of OCT signals at other imaging positions, and thus it is possible to rapidly acquire motion contrast data which requires time to acquire. As in the present example, the calculation process is performed whenever an OCT signal is acquired at each crossing position, and thus it is possible to perform calculation by taking into consideration deviations in the crossing direction (X direction) and the depth direction (Z direction) and thus to acquire highly accurate functional OCT image data. The technique of the present disclosure is more useful in acquisition of three-dimensional functional OCT image data. In other words, when three-dimensional functional OCT image data is acquired, since it is necessary to detect OCT signals at a plurality of crossing positions and to perform a process, it takes long time to acquire three-dimensional functional OCT, and thus the technique of the present disclosure becomes more useful.

In the present example, a description has been made of an example of a case where motion contrast data is acquired in a scanning line (crossing position), but the present example is not limited thereto. The control unit 70 may process a plurality of OCT signals acquired at the first position so as to acquire motion contrast data at the first position during acquisition of a plurality of OCT signals at the second position. For example, the first position and the second position may be a single position (A scan line).

In the present example, motion contrast data may be displayed on the monitor 75 whenever the motion contrast data is acquired. For example, the control unit 70 acquires functional OCT image data in the first scanning line S1 and also displays the functional OCT image data on the monitor 75. With this configuration, the examiner can check whether or not acquisition of motion contrast data has been acquired with high accuracy at an imaging position at which acquisition of an OCT signal has been completed before completing acquisition of OCT signals at all set imaging positions. For this reason, for example, the examiner can perform consecutive re-imaging at an imaging position at where favorable motion contrast data is not acquired, and can thus reduce time and effort for re-imaging after imaging is completed.

In the present example, the control unit 70 may determine whether or not motion contrast data is appropriate, and may output determination information based on a determination result. For example, the control unit 70 may determine whether or not motion contrast data is appropriate based on signal intensity (for example, the magnitude of a luminance value) of acquired motion contrast data. In addition, for example, the control unit 70 may acquire an OCT image corresponding to each OCT signal based on a plurality of OCT signals which are acquired in the same scanning line and are used to acquire motion contrast data, and may determine whether or not motion contrast data is appropriate based on a correlation value (similarity) between the acquired OCT images. For example, as a configuration of outputting determination information, there may be a configuration of outputting a signal for transfer to the next operation. In this case, for example, in a case where there control unit 70 determines that there is an imaging position where motion contrast data is determined not to be appropriately acquired, the control unit 70 may perform re-imaging at the imaging position where motion contrast data is determined not to be appropriately acquired. For example, as a configuration of outputting determination information, there may be a configuration of outputting error information indicating that an imaging position is present at which motion contrast data is not appropriately acquired (for example, the error information is displayed on the monitor 75 or is printed), or a configuration of outputting guide information for prompting re-imaging. With this configuration, even in a case where favorable motion contrast data has not been acquired, transfer to the next operation can be smoothly made. The examiner can easily confirm that favorable motion contrast data has not been acquired.

The control unit 70 may update motion contrast data whenever the motion contrast data is acquired, and may display the motion contrast data of a moving image on the monitor 75. For example, the control unit 70 acquires motion contrast data at each position and also sequentially displays the motion contrast data on the monitor 75. For example, in a case where three-dimensional functional OCT image data is updated, the control unit 70 updates motion contrast data in each scanning line whenever the motion contrast data is acquired in each set scanning line. Of course, OCT functional enface image data which is acquired based on motion contrast data may be updated. In this case, for example, the control unit 70 sequentially acquires three-dimensional motion contrast data, sequentially acquires OCT functional enface image data based on the three-dimensional motion contrast data, and updates the OCT functional enface image data in each scanning line (each crossing position). Consequently, the examiner can identify the three-dimensional functional OCT image data of a moving image (real time) and the OCT functional enface image data in real time on the monitor 75.

In addition, a position where imaging is performed may be set by identifying the motion contrast data or the OCT functional enface image data which is updated in real time. For example, the control unit 70 can set a position where imaging is performed based on real-time three-dimensional functional OCT image data or OCT functional enface image data which is displayed on the monitor 75. The control unit 70 controls scanning means for applying measurement light so that image data is acquired at a set acquisition position. In this case, for example, an acquisition position of tomographic image data can be set based on real-time three-dimensional functional OCT image data or OCT functional enface image data, and the scanning means for applying measurement light may be controlled so that image data is acquired at the set acquisition position. With this configuration, the examiner can easily acquire image data of a part which is more specifically identified in a state in which the real-time motion contrast data or OCT functional enface image data is identified. Of course, the examiner may not set an acquisition position of tomographic image data but the control unit 70 may automatically set an acquisition position of the tomographic image data. In this case, for example, the control unit 70 sets an acquisition position based on blood vessel analysis information to be described later so that tomographic image data of a region where a large number of blood vessels are present is acquired. In addition, an indication (for example, a line indication) representing an acquisition position of tomographic image data may be set based on real-time three-dimensional functional OCT image data or OCT functional enface image data.

<Correlation of Three-Dimensional Functional OCT Enface Image Data>

If the three-dimensional functional OCT image data of the subject's eye is acquired in the above-described manner, the control unit 70 correlates the three-dimensional functional OCT image data and other fundus image data with each other. For example, the control unit 70 correlates the three-dimensional functional OCT image data and other fundus image data with each other by performing a matching process. Hereinafter, correlation between images will be described. In addition, in the present example, as other fundus image data with which three-dimensional functional OCT image data is correlated, enface image data (hereinafter, referred to as SLO enface image data) acquired by an SLO will be described as an example. Of course, as other fundus image data with which three-dimensional functional OCT image data is correlated, various items of fundus image data may be employed.

Figure 4:
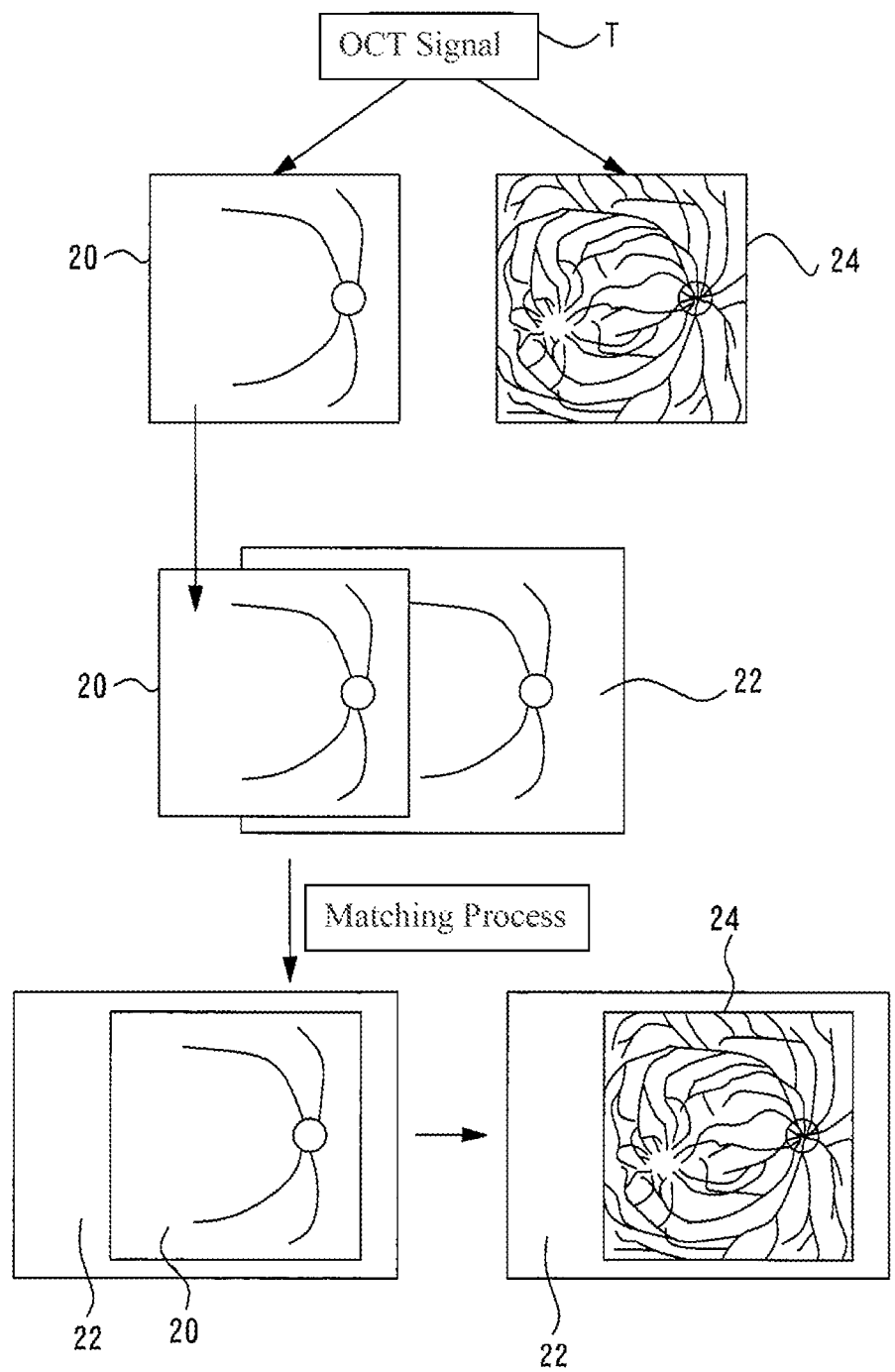
FIG. 4 is a diagram illustrating correlation of three-dimensional functional OCT image data.

FIG. 4 is a diagram illustrating correlation of three-dimensional functional OCT image data. Hereinafter, with reference to FIG. 4, a description will be made of an image analysis process for correlating positions of three-dimensional functional OCT image data and SLO enface image data with each other.

In the following description of the correlation, as an example, a description will be made of a case where OCT functional enface image data 24 which is acquired based on three-dimensional functional OCT image data is correlated with SLO enface image data 22. In the present example, the control unit 70 acquires the OCT functional enface image data 24 which is enface image data in a predetermined depth region of the subject based on three-dimensional functional OCT image data. For example, in a case of acquiring the OCT functional enface image data 24, the control unit 70 integrates the three-dimensional functional OCT image data in the depth direction so as to acquire the OCT functional enface image data 24. Of course, the OCT functional enface image data 24 may be acquired, as described above, through integration of spectral data at respective XY positions, extraction of luminance data at respective XY positions in a certain depth direction, or the like. For example, the OCT functional enface image data 24 in the predetermined depth region may be OCT functional enface image data which is acquired in all regions (for example, all retinal layers) in the depth direction of the OCT functional enface image data, or some of the retinal layers (for example, at least one of the retinal layers, or a plurality of layers of the retinal layers) in the depth direction of the three-dimensional functional OCT image data.

In the present example, the matching process is performed based on a plurality of OCT signals T which are used to acquire the three-dimensional functional OCT image data and are temporally different from each other with respect to the same position. For example, the control unit 70 processes a plurality of OCT signals T acquired at a plurality of positions on the subject's eye so as to process at least one OCT signal at each of the plurality of positions, and thus acquires enface image data (reference enface image data) 20 of the subject, for being used as a reference image in the matching process. For example, the control unit 70 uses OCT enface image data (tomographic image data obtained in a two-dimensional manner) as the reference enface image data 20.

For example, in a case where the OCT enface image data is acquired, the control unit 70 integrates three-dimensional OCT image data in the depth direction so as to acquire OCT enface image data. Of course, the OCT enface image data may be acquired, as described above, by using an integrated value of spectral data at respective XY positions, through extraction of luminance data at respective XY positions in a certain depth direction, or the like.

The control unit 70 matches the reference enface image data (hereinafter, referred to as OCT enface image data) 20 with the SLO enface image data 22 so as to correlate the SLO enface image data 22 with the OCT functional enface image data 24 based on the three-dimensional functional OCT image data.

For example, as the matching process, the control unit 70 detects a positional deviation between the OCT enface image data 20 and the SLO enface image data 22, and correlates positions of the OCT functional enface image data 24 and the SLO enface image data 22 with each other based on the positional deviation.

For example, as a method of detecting a positional deviation between two images, various image processing methods (a method using various correlation functions, a method using Fourier transform, and a method based on matching of feature points) may be used.

For example, a method may be used in which positions of predetermined reference image data (for example, the OCT enface image data 20) or target image data (the SLO enface image data 22) are deviated by one pixel, and a positional deviation between both the data items when both the data items match each other most (when the correlation becomes highest) by comparing the reference image with the target image. In addition, a method may be used in which a common feature point is extracted from a predetermined reference image and target image, and a positional deviation of the extracted feature point is detected.

As a function for obtaining a phase difference between two image data items, a phase restricting correlation function may be used. In this case, first, Fourier transform is performed on each image data item, and a phase and amplitude of each frequency component are obtained. In addition, the obtained amplitude component is normalized to the magnitude "1" with respect to the respective frequency components. Next, a phase difference for each frequency between the two image data items is calculated, and inverse Fourier transform is performed thereon.

Here, if there is no positional deviation between the two image data items, only cosine waves are added together, and a peak appears at the origin position (0,0). In addition, if there is a positional deviation, a peak appears at a position corresponding to the positional deviation. Therefore, if a peak detection position is obtained, a positional deviation between two image data items can be obtained. According to this method, it is possible to detect a positional deviation between the OCT enface image data 20 and the SLO enface image data 22 with high accuracy and in a short time period.

In the present example, the control unit 70 uses a method in which a common feature point is extracted from the OCT enface image data 20 and the SLO enface image data 22, and a positional deviation of the extracted feature point is detected. If the positional deviation is detected, the control unit 70 correlates positions of the OCT functional enface image data 24 and the SLO enface image data 22 with each other based on the positional deviation.

Here, the OCT enface image data 20 and the OCT functional enface image data 24 are acquired based on the same OCT signal T, and thus both the data items can be correlated with each other in a pixel-to-pixel relationship. For this reason, a positional deviation does not occur much in a positional relationship between the OCT enface image data 20 and the OCT functional enface image data 24. Therefore, since positions of the OCT enface image data 20 and the OCT functional enface image data 24 are not required to be correlated with each other again, a positional deviation between the OCT enface image data 20 and the SLO enface image data 22 can be applied as a positional deviation between the OCT functional enface image data 24 and the SLO enface image data 22. Thus, correlation between respective image data items are not required to be performed plural times, and the OCT functional enface image data 24 can be easily correlated with the SLO enface image data 22 with high accuracy.

If the correlation is completed, the control unit 70 displays the OCT functional enface image data 24 and the SLO enface image data 22 in a superimposed manner. In addition, in the present example, an example of a configuration in which the OCT functional enface image data 24 and the SLO enface image data 22 are displayed in a superimposed manner, but the present example is not limited thereto. For example, the control unit 70 may display the OCT functional enface image data 24 and the SLO enface image data 22 in parallel. In this case, for example, a position where the OCT functional enface image data has been acquired may be displayed (displayed using an electronic display mark or the like) on the SLO enface image data.

As described above, since reference enface image data used for the matching process and three-dimensional functional OCT image data used for an angiographic image can be acquired based on an OCT signal, even if there is a difference in the type of image data (for example, a luminance distribution, contrast, a resolution, and a form of a test substance) from other enface image data which is correlated with the three-dimensional functional OCT image data, the correlation can be easily performed with high accuracy. In addition, if three-dimensional functional OCT image data used for an angiographic image is correlated with other fundus image data, a relationship of both of the data items can be easily identified, and thus information useful for diagnosis can be acquired.

In addition, in the present example, a description has been made of an example of a configuration in which the SLO enface image data 22 and the OCT functional enface image data 24 are displayed in a superimposed manner, but the present example is not limited thereto. The technique of the present disclosure is applicable to information which can be acquired based on three-dimensional functional OCT image data. For example, the three-dimensional functional OCT image data and the SLO enface image data 22 may be displayed in a superimposed manner. In addition, for example, analysis information (details thereof will be described later) obtained by analyzing the three-dimensional functional OCT image data and the SLO enface image data 22 may be displayed in a superimposed manner.

In the present example, a description has been made of an example of a configuration in which the matching process is performed on the SLO enface image data 22 by using the OCT enface image data 20 which is acquired based on the OCT signal T, but the present example is not limited thereto. A different type of enface image data may be created based on the OCT signal T, and functional enface image data to be used for a matching process may be selected depending on enface image data which is correlated with three-dimensional functional OCT image data.

For example, the control unit 70 uses at least one of OCT enface image data which is acquired based on at least one of a plurality of OCT signals acquired at a plurality of positions on the subject's eye, and OCT functional enface image data which is acquired based on three-dimensional functional OCT image data, as functional enface image data. The control unit 70 selects at least one of OCT enface image data and OCT functional enface image data as reference enface image data for being correlated with other fundus image data depending on enface image data (for example, other fundus image data) which is to be correlated with three-dimensional functional OCT image data. The control unit 70 matches at least one of the OCT enface image data and the OCT functional enface image data with the enface image data. Consequently, correlation with the three-dimensional functional OCT image data is preformed. As mentioned above, reference enface image data used for the matching process is changed depending on enface image data to be correlated with the three-dimensional functional OCT image data, and thus correlation with image data with similarity (for example, similarity of a luminance distribution, similarity of contrast, similarity of a resolution, and similarity of a form of a test substance) to image data can be performed. Therefore, accuracy of the correlation can be further improved. Of course, the examiner may operate the operation unit 76 so as to select an image to be used as reference enface image data.

In the present example, a description has been made of an example of a configuration in which three-dimensional functional OCT image data is correlated with other fundus image data, but the present example is not limited thereto. For example, the technique of the present disclosure is applicable to correlation between motion contrast data (for example, functional OCT image data) and other fundus image data.

In the present example, in order to acquire motion contrast data, more favorable OCT image data or three-dimensional OCT image data may be acquired by using two or more acquired OCT signals which are temporally different from each other at the same position. For example, since two or more OCT signals are acquired in relation to the same part, composite processes (for example, an integration process, an adding process, and the like) are performed on the OCT signals. For example, in a case where the adding process is performed, the control unit 70 performs an adding position on a plurality of OCT signals acquired at a plurality of positions on the subject's eye, and acquires image data having undergone the adding process at the plurality of positions on the subject's eye.

In the present example, when a matching process is performed with wide range enface image data (for example, panorama image data acquired by a fundus camera) as other fundus image data, the matching process is more preferably performed based on at least one of fixation target information and scanning position information. In this case, since a region corresponding to three-dimensional functional OCT image data is identified based on fundus image data in a wide range, a range for the checking can be further narrowed by using at least one of the fixation target information and the scanning position information. Consequently, display indicating three-dimensional functional OCT image data can also be easily superimposed on a wider range fundus image with high accuracy.

In the present example, the control unit 70 may correlate three-dimensional functional OCT image data used for an angiographic image with other fundus image data and then may display an indication (for example, a line indication) representing an acquisition position of three-dimensional OCT image data on other fundus image data. In the above-described way, acquisition positions of tomographic image data can be identified on various enface images, and thus it is possible to acquire information useful for diagnosis.

<Acquisition of Analysis Information>

In the present example, acquired motion contrast data is analyzed so that blood vessel position information is acquired, and analysis information regarding the blood vessel is acquired based on the position information. Hereinafter, a description will be made of a case where motion contrast data is analyzed, and analysis information regarding a blood vessel is acquired. For example, the control unit 70 determines whether or not there is a blood vessel in a region in the depth direction of acquired motion contrast data, and acquires analysis information based on a determination result. For example, as the region in the depth direction, used to determines whether or not a blood vessel is present, a determination process is performed throughout all regions of the retinal layers of the subject's eye.

Hereinafter, as an example, a description will be made of a case where three-dimensional functional OCT image data is analyzed as motion contrast data. For example, the control unit 70 analyzes acquired three-dimensional functional OCT image data so as to acquire blood vessel position information. The control unit 70 acquires analysis information regarding the blood vessel based on the acquired blood vessel position information.

For example, the control unit 70 determines whether or not a blood vessel is present in a region in the depth direction of the three-dimensional functional OCT image data, and acquires analysis information based on a determination result. In addition, in the following description, in a case where an analysis process is performed on imaging data at one crossing position in three-dimensional functional OCT image data, and the three-dimensional functional OCT image data, for example, analysis of respective functional OCT image data items forming the three-dimensional functional OCT image data is sequentially performed, and thus the three-dimensional functional OCT image data is analyzed.

Figure 5A:
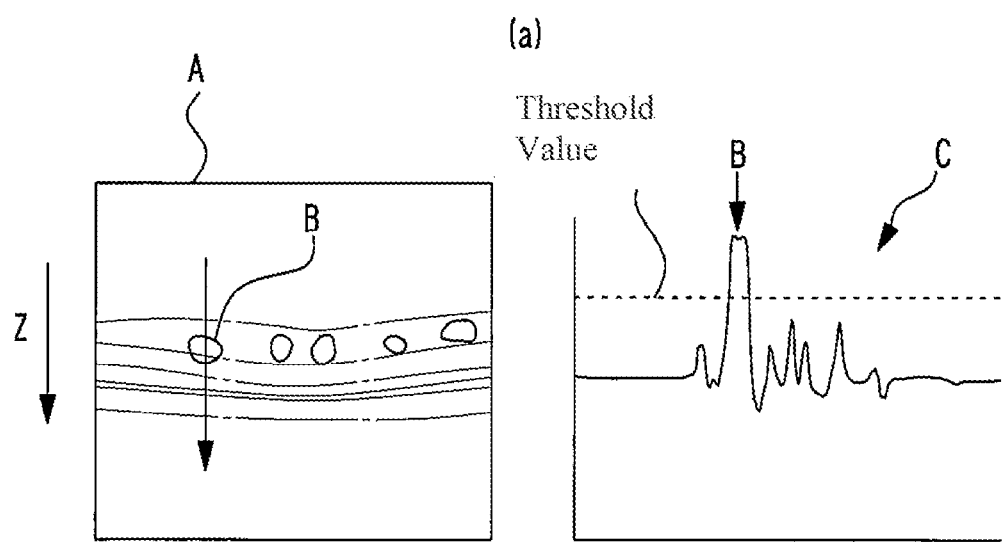
FIGS. 5A and 5B are a schematic diagram illustrating functional OCT image data acquired by the OCT optical system and an example of a luminance distribution thereof.
Figure 5B:
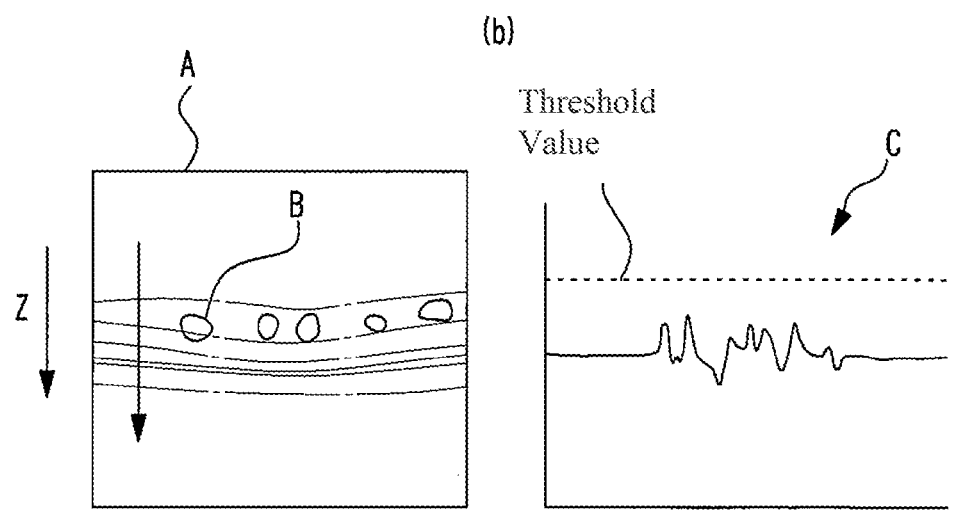

FIGS. 5*a* and 5*b* is a schematic diagram illustrating functional OCT image data A acquired by the OCT optical system 100 and an example of a luminance distribution C thereof. The control unit 70 performs a determination process on a blood vessel B in each functional OCT image data item A of three-dimensional functional OCT image data. The control unit 70 processes the functional OCT image data A so as to determine whether or not the blood vessel B is present in a two-dimensional manner, and acquires analysis information based on a determination result. The control unit 70 detects the blood vessel B of the fundus in the acquired functional OCT image data A through image processing, and also determines whether or not the blood vessel B is present based on a predetermined determination condition (determination criterion). The control unit 70 obtains analysis information regarding the functional OCT image data A based on a determination result.

In a case where the determination process is performed by processing functional OCT image data, the control unit 70 may determine whether or not a blood vessel is present by performing the process in each A scan line forming the functional OCT image data, and may determine whether or not a blood vessel is present by processing the entire functional OCT image data.

<Determination of Presence or Absence of Blood Vessel>

In a case where the presence or absence of the blood vessel B is determined by detecting a blood vessel position, for example, a luminance level is detected in the depth direction of the functional OCT image data A, and the blood vessel B present in the retinal layer is extracted through image processing (for example, detection of an edge).

In a case where the presence or absence of the blood vessel B is determined based on the functional OCT image data A, for example, the control unit 70 detects a luminance distribution C of each A scan signal in the depth direction (Z direction) (on a scanning line Z1 in FIGS. 5a and 5b), and determines whether or not the presence or absence of the blood vessel B based on whether or not a luminance value exceeding a predefined threshold value is detected. For example, it is determined that a blood vessel is present at a position where a detected luminance value exceeds the threshold value. For example, the threshold value may be set in advance by calculating a luminance value corresponding to a blood vessel. With this configuration, a luminance change caused by noise or the like and a luminance change caused by a blood vessel can be easily differentiated from each other, and a blood vessel part can be extracted with high accuracy. A method of detecting a blood vessel position is not limited to the above-described configuration. For example, the control unit 70 may determine a portion where a luminance value is detected as a portion where a blood vessel is present.

FIG. 5(a) illustrates an example of the luminance distribution C in a state in which the blood vessel B is present on the scanning line Z1, and FIG. 5(b) illustrates an example of the luminance distribution C in a state in which the blood vessel B is not present on the scanning line Z1. In other words, in a case where the blood vessel B is present, a luminance value corresponding to the blood vessel B can be observed, but in a case where the blood vessel B is not present, a luminance value corresponding to the blood vessel B cannot be observed. In the above-described way, the control unit 70 performs two-dimensional determination regarding the presence or absence of the blood vessel B on the fundus of the subject's eye so as to obtain two-dimensional information of the fundus regarding the presence or absence of the blood vessel B.

In a case where analysis information using three-dimensional functional OCT image data is acquired, the control unit 70 analyzes functional OCT image data which is acquired at each of a plurality of crossing positions on the subject's eye so as to acquire analysis information regarding a blood vessel. Consequently, the analysis information using the three-dimensional functional OCT image data is acquired. In other words, in the above-described determination process regarding the presence or absence of a blood vessel, the control unit 70 performs the determination process with respect to a plurality of different positions on the fundus so as to acquire the analysis information using the three-dimensional functional OCT image data.

<Creation of Analysis Map>

Figure 6:
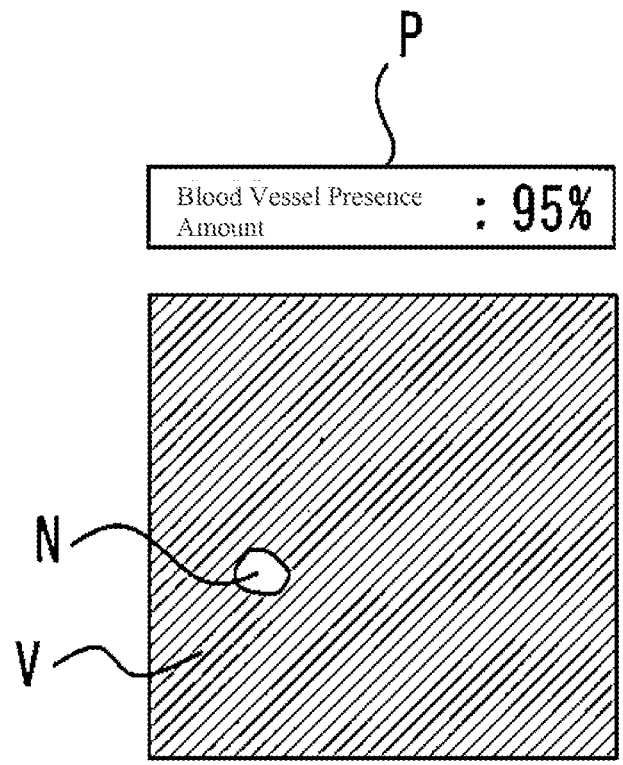
FIG. 6 is a diagram illustrating an analysis map and an analysis parameter.

FIG. 6 is a diagram illustrating an analysis map and an analysis parameter. In the present example, for example, the control unit 70 acquires an analysis map indicating distribution states (two-dimensional distribution) of a blood vessel region V where it is determined that a blood vessel is present and a non-blood vessel region N where it is determined that a blood vessel is not present, as analysis information, based on the determination result obtained as described above. For example, the control unit 70 acquires an analysis parameter P based on the determination result obtained as described above as analysis information. For example, in a case of acquiring the analysis map and the analysis parameter, the analysis map and the analysis parameter are acquired based on a determination result of three-dimensional functional OCT image data.

For example, the control unit 70 calculates the analysis parameter P based on a presence amount of at least one of the blood vessel region V and the non-blood vessel region N in a predetermined fundus region based on a determination result. For example, a ratio of the blood vessel region V and the non-blood vessel region N in a predetermined imaging region is calculated as the analysis parameter P. Consequently, an amount of blood vessels which are present in a predetermined region is confirmed.

The analysis parameter may be at least one of dimension information (length information), area information, and volume information (a volume, a volume ratio, or the like which is actually calculated) of a blood vessel region in a predetermined fundus region based on a determination result. In addition, the analysis parameter may be an analysis parameter based on at least one of dimension information, area information, and volume information of a non-blood vessel region in a predetermined fundus region. For example, an actually calculated area may be displayed as the area information. The number of pixels in which a blood vessel is present may be calculated as a parameter. The volume information is calculated by using an area and information (for example, the thickness of a blood vessel) in the depth direction, the information in the depth direction corresponding to a region for calculation of the area and being acquired based on three-dimensional functional OCT image data. A three-dimensional analysis map (color three-dimensional map) can be created and displayed by using volume information of each layer. In addition, the dimension information is calculated by using information in the vertical direction and the horizontal direction of the analysis map. Of course, the area information, the volume information, and the dimension information may all be displayed. In the present example, a numerical value is displayed as a parameter indicating an amount of blood vessels which are present, but the present example is not limited thereto. Not only a numerical value but also a bar graph, a radar chart, or the like may be displayed.

Figure 7:
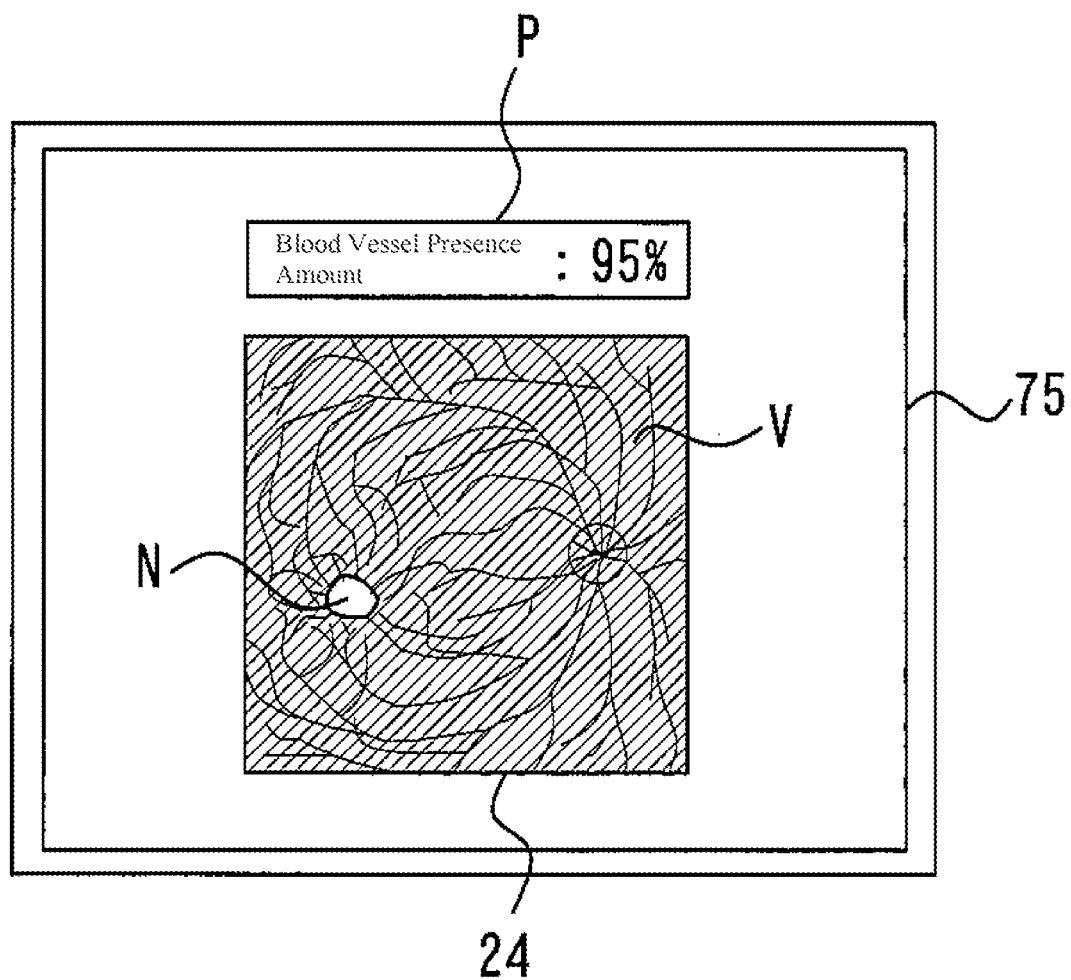
FIG. 7 is a diagram illustrating an example in which motion contrast data and analysis information are displayed in a superimposed manner.

If the analysis information regarding a blood vessel is acquired in the above-described way, the control unit 70 displays motion contrast data and the analysis information regarding a blood vessel on the monitor 75 in a superimposed manner (refer to FIG. 7). For example, in a case where analysis information using three-dimensional functional OCT image data is acquired, the control unit 70 displays OCT functional enface image data which is acquired based on the three-dimensional functional OCT image data and corresponds to a region in a predetermined depth direction, and the analysis information in a superimposed manner. Of course, the three-dimensional functional OCT image data and the analysis information may be displayed in a superimposed manner.

As mentioned above, since analysis information regarding a blood vessel can be compared with motion contrast data, the examiner can perform appropriate diagnosis while easily comparing various information pieces with each other. In addition, since a non-blood vessel region can be easily identified, it is possible to detect a retinal disease such as ischemia early.

In the present example, a description has been made of an example of a configuration in which a determination process is performed in all regions of the retinal layers of the subject's eye as a region in the depth direction when determination of the presence or absence of a blood vessel is performed, but the present example is not limited thereto. It may be determined whether or not a blood vessel is present in some regions in the depth direction of motion contrast data, and analysis information based on a determination result may be acquired. For example, the control unit 70 analyzes OCT image data or three-dimensional OCT image data which is acquired by using an OCT signal, and detects respective retinal layers (for example, a nerve fiber layer (NFL), a ganglion cell layer (GCL), and a retinal pigment epithelium (RPE)). The control unit 70 determines whether or not a blood vessel is present between predetermined layer boundaries so as to acquire analysis information. With this configuration, the examiner can understand a blood vessel distribution in a specific layer or between layers and can thus perform more appropriate diagnosis. For example, since the presence of a blood vessel can be identified in the RPE layer, a newborn blood vessel can be easily detected early, and thus it becomes easier to detect lesions. In addition, the examiner can confirm an effect of a drug in a specific layer or between layers, or an effect of laser treatment.

In the present example, a description has been made of an example of a configuration in which motion contrast data and analysis information regarding a blood vessel are displayed in a superimposed manner, but the present example is not limited thereto. The motion contrast data and the analysis information have only to be displayed so as to be compared with each other. For example, as a configuration in which the motion contrast data and the analysis information are displayed so as to be compared with each other, there may be a configuration in which the motion contrast data and the analysis information are displayed in parallel.

In the present example, a description has been made of an example of a configuration in which motion contrast data and analysis information regarding a blood vessel are displayed on the monitor 75, but the present example is not limited thereto. The motion contrast data and the analysis may be output. For example, as a configuration in which the motion contrast data and the analysis are output so as to be compared with each other, there may be a configuration in which the motion contrast data and the analysis information are printed, or a configuration in which data including the motion contrast data and the analysis information is transmitted.

In the present example, a description has been made of an example of a configuration in which motion contrast data and analysis information regarding a blood vessel are displayed in a superimposed manner, but the present example is not limited thereto. Enface image data acquired by the enface observation optical system 200 and analysis information may be displayed so as to be compared with each other. In this case, for example, enface image data acquired by the enface observation optical system 200 and analysis information may be displayed so as to be compared with each other. For example, motion contrast data, enface image data acquired by the enface observation optical system 200, and analysis information may be displayed so as to be compared with each other. For example, in a case where analysis is superimposed on enface image data acquired by the enface observation optical system 200, the control unit 70 acquires OCT enface image data based on an OCT signal which is used to acquire three-dimensional functional OCT image data. The control unit 70 correlates the OCT enface image data with enface image data acquired by the enface observation optical system 200 through a matching process. The three-dimensional functional OCT image data and the OCT enface image data are acquired based on the same OCT signal, and thus both the data items can be correlated with each other in a pixel-to-pixel relationship. In addition, analysis information is acquired based on the three-dimensional functional OCT image data, and thus both the data items can be correlated with each other in a pixel-to-pixel relationship. Consequently, the analysis information can be correlated with the enface image data acquired by the enface observation optical system 200.

Figure 8:
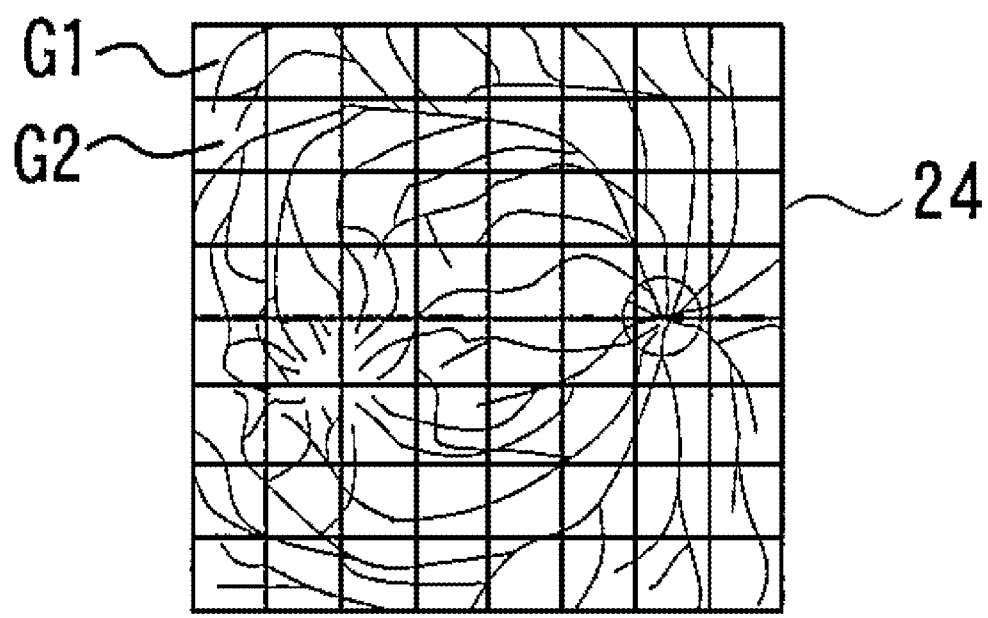
FIG. 8 is a diagram illustrating a case where a fundus region is divided in order to acquire analysis information.

In the present example, a description has been made of an example of a configuration in which a blood vessel determination process is performed in the A scan units and thus analysis information using three-dimensional functional OCT image data is acquired, but the present example is not limited thereto. For example, the three-dimensional functional OCT image data may be divided into a plurality of regions, and a blood vessel determination process may be performed for each divided region so that analysis information using the three-dimensional functional OCT image data is acquired. FIG. 8 is a diagram illustrating a case where a fundus region is divided in order to acquire analysis information. For example, the control unit 70 divides three-dimensional functional OCT image data into a plurality of regions (for example, a plurality of regions on an XY plane (fundus plane)). The control unit 70 determines whether or not a blood vessel is present in each divided region for each divided region (for example, refer to divided regions G1 and G2 in FIG. 8). The control unit 70 acquires analysis information based on a determination result. In a case where a determination process is performed for each divided region, for example, if blood vessels are present at a plurality of positions in the divided region, the control unit 70 may determine that blood vessels are present in the divided region. For example, in a case where it is determined that blood vessels are consecutively present within a predetermined range in the divided region, it may be determined that blood vessels are present in the divided region. As mentioned above, since a blood vessel determination process is performed for each divided region, a blood vessel and noise or the like can be differentiated from each other with higher accuracy. In other words, it is possible to prevent accuracy of blood vessel determination from being reduced due to an influence of noise or the like.

In addition, analysis information regarding a blood vessel may be output (for example, printing, display, and data transmission) so as to be compared with a layer analysis map which is obtained by analyzing the retinal layer of the fundus. For example, the control unit 70 detects layer information by using an OCT signal which is acquired in order to acquire three-dimensional functional OCT image data, and acquires a layer analysis map (for example, a difference map or a layer thickness map) indicating a two-dimensional distribution regarding layer thickness information of the retinal layer of the subject's eye. The control unit 70 displays the analysis information regarding a blood vessel and the layer analysis map obtained by analyzing the retinal layer of the fundus on the monitor 75 in a superimposed manner. Of course, the analysis information regarding a blood vessel and the layer analysis map obtained by analyzing the retinal layer of the fundus may be displayed in parallel. With this configuration, the examiner can easily identify a relationship between both a state of the retinal layer and a state of a blood vessel, and can thus perform more appropriate diagnosis.

The present invention is not limited to the devices disclosed in the present example. For example, optical coherence tomography calculation software (program) for executing the functions of the above-described example is provided to the system or the device via a network, various recording media, or the like. A computer (for example, a CPU) of the system or the device may read and execute the program.

In the present example, a description has been made of a configuration in which a test substance is the eye, but the present example is not limited thereto. The technique of the present disclosure is also applicable to an optical coherence tomography device which images test substances such as living bodies (for example, a skin or a blood vessel) other than the eye, or samples other than the living bodies.

What is claimed is:

1. An optical coherence tomography (OCT) device comprising:
a processor; and
a memory storing a computer program, when executed by the processor, causing:
an acquisition unit of the OCT device to acquire a plurality of OCT signals which are temporally different from each other with respect to a same position on a test substance for each of a plurality of positions on the test substance;
a calculation unit of the OCT device to process the plurality of OCT signals acquired at the plurality of positions on the test substance so as to acquire three-dimensional OCT motion contrast data of the test substance;
an image processing unit of the OCT device to generate OCT images corresponding to the respective OCT signals acquired at a same scanning line and determining motion contrast data based on a similarity threshold correspondence between the OCT images based on which the motion contrast data is generated; and
control of the acquisition unit to perform re-imaging when the similarity threshold correspondence is not obtained in the image processing.

2. The optical coherence tomography device according to claim 1,
wherein the acquisition unit acquires the plurality of OCT signals at a first position on the test substance and then acquires the plurality of OCT signals at a second position which is different from the first position, and
wherein the calculation unit processes the plurality of OCT signals acquired at the first position so as to acquire motion contrast data at the first position while the acquisition unit acquires the plurality of OCT signals at either or both of the first position and the second position.

3. The optical coherence tomography device according to claim 2,
wherein the first position is a first crossing position, and the second position is a second crossing position, and
wherein the calculation unit processes the plurality of OCT signals acquired at the first crossing position so as to acquire motion contrast data at the first crossing position while the plurality of OCT signals are acquired at either or both of the first crossing position and the second crossing position.

4. The optical coherence tomography device according to claim 3,
wherein the acquisition unit scans, with measurement light, a plurality of different crossing positions of the test substance so as to acquire the OCT signal for acquiring three-dimensional motion contrast data regarding XY directions, and
wherein the calculation unit processes OCT signals at the plurality of crossing positions so as to acquire the three-dimensional motion contrast data.

5. The optical coherence tomography device according to claim 2,
wherein acquisition unit scans, with measurement light at a plurality of different crossing positions of the test substance so as to acquire the OCT signal for acquiring three-dimensional motion contrast data regarding XY directions,
wherein the calculation unit processes OCT signals at the plurality of crossing positions so as to acquire the three-dimensional motion contrast data, and
wherein the computer program, when executed by the processor, further causes:
an analysis processing unit to sequentially acquire the three-dimensional motion contrast data, sequentially acquiring OCT motion contrast enface image data which is enface image data in a predetermined depth region of the test substance based on the three-dimensional motion contrast data, and sequentially displaying the OCT motion contrast enface image data at each crossing position on a display unit to display real-time OCT motion contrast enface image data on the display unit.

6. The optical coherence tomography device according to claim 1,
wherein the calculation unit processes the plurality of acquired OCT signals so as to acquire motion contrast data of a subject's eye, and
wherein the computer program, when executed by the processor, further causes:
an analysis processing unit to process the acquired motion contrast data so as to acquire position information of a blood vessel, and acquiring analysis information regarding the blood vessel based on the position information.

7. The optical coherence tomography device according to claim 6,
wherein the analysis processing unit processes the motion contrast data as the analysis information so as to determine whether or not the blood vessel is present, and acquires the analysis information based on a determination result.

8. The optical coherence tomography device according to claim 7,
wherein the analysis processing unit processes the motion contrast data so as to determine whether or not the blood vessel is present in a region in a depth direction of the motion contrast data, and acquires analysis information based on a determination result.

9. The optical coherence tomography device according to claim 6,
wherein the acquisition unit scans, with measurement light, a plurality of different crossing positions on the subject's eye so as to acquire the OCT signal for acquiring three-dimensional OCT motion contrast data regarding XY directions,
wherein the calculation unit processes the plurality of OCT signals acquired at the plurality of crossing positions on the subject's eye so as to acquire the three-dimensional OCT motion contrast data as the motion contrast data of the subject's eye, and wherein the analysis processing unit processes the three-dimensional OCT motion contrast data so as to acquire analysis information regarding a blood vessel for each position on the subject's eye as the analysis information, acquires OCT motion contrast enface image data which is the enface image data in a predetermined depth region of the test substance based on the three-dimensional OCT motion contrast data, and outputs the OCT motion contrast enface image data and the analysis information in such a manner that the OCT motion contrast enface image data can be compared with the analysis information.

10. The optical coherence tomography device according to claim 9, wherein the analysis processing unit divides the three-dimensional OCT motion contrast data into a plurality of regions so as to determine whether or not the blood vessel is present in each divided region for each divided region, and acquires analysis information based on a determination result.

11. The optical coherence tomography device according to claim 6, wherein the acquisition unit scans, with measurement light, a plurality of different crossing positions on the subject's eye so as to acquire an OCT signal for acquiring three-dimensional OCT motion contrast data regarding XY directions, wherein the calculation unit processes the plurality of OCT signals acquired at the plurality of crossing positions on the subject's eye so as to acquire the three-dimensional OCT motion contrast data as the motion contrast data of the subject's eye, and wherein the analysis processing unit processes the three-dimensional OCT motion contrast data so as to acquire analysis information regarding a blood vessel for each position on the subject's eye as the analysis information, and displays the three-dimensional OCT motion contrast data and the analysis information in such a manner that the three-dimensional OCT motion contrast data can be compared with the analysis information.

12. The optical coherence tomography device according to claim 1, wherein when the image processing unit determines that the motion contrast data is not appropriate, the acquisition unit causes the optical coherence tomography device to acquire the plurality of OCT signals again at the position where motion contrast data is determined not to be appropriate.

13. The optical coherence tomography device according to claim 1, wherein the image processing unit determines whether the motion contrast data is appropriate or not based on a signal intensity of the acquired motion contrast data.

14. The optical coherence tomography device according to claim 1, wherein the image processing unit causes the optical coherence tomography device to display analysis information regarding a blood vessel in a superimposed manner on an enface image data acquired by an enface image acquisition unit configured to acquire enface image data of the test substance.

15. The optical coherence tomography device according to claim 1, wherein the image processing unit causes the optical coherence tomography device to display the motion contrast data and analysis information regarding a blood vessel based on the motion contrast data in a superimposed manner on an enface image data acquired by an enface image acquisition unit configured to acquire enface image data of the test substance.

16. The optical coherence tomography device according to claim 1, wherein the image processing unit causes the optical coherence tomography device to display a layer analysis map regarding layer thickness information of the test substance and analysis information regarding a blood vessel based on the motion contrast data in a superimposed manner or in parallel manner.

17. The optical coherence tomography device according to claim 1, wherein the image processing unit causes the optical coherence tomography device to superimpose a three-dimensional OCT image data on enface image data acquired by an enface image acquisition unit configured to acquire enface image data of the test substance based on at least one of fixation target information and scanning position information.

18. The optical coherence tomography device according to claim 1, wherein when the motion contrast data is determined not to be appropriate, the device displays error information to inform an operator of the device.

19. The optical coherence tomography device according to claim 1, wherein, in the image processing unit, OCT images in a depth direction is taken into account when determining whether motion contrast data is based on the similarity between the acquired OCT images.

20. An optical coherence tomography calculation method comprising:
acquiring a plurality of OCT signals which are temporally different from each other with respect to the same position on a test substance for each of a plurality of positions on the test substance;
processing the plurality of acquired OCT signals so as to acquire three-dimensional OCT motion contrast data of the test substance;
acquiring OCT images corresponding to the respective OCT signals acquired at the same scanning line; and
determining motion contrast data based on a similarity threshold correspondence between the acquired OCT images based on which the motion contrast data is generated; and
re-imaging at an imaging position when the similarity threshold correspondence is not obtained.

21. A non-transitory computer readable recording medium storing an optical coherence tomography calculation program executed in a control device which controls an operation of an optical coherence tomography device, the program being executed by a processor of the control device so as to cause:
an acquisition unit of the OCT device to acquire a plurality of OCT signals which are temporally different from each other with respect to the same position on a test substance for each of a plurality of positions on the test substance;
a calculation unit of the OCT device to process the plurality of acquired OCT signals so as to acquire three-dimensional OCT motion contrast data of the test substance;
an image processing unit of the OCT device to generate OCT images corresponding to the respective OCT signals acquired at the same scanning line; and determine motion contrast data based on a similarity threshold correspondence between the OCT images based on which the motion contrast data is generated; and control of the acquisition unit to perform re-imaging when the similarity threshold correspondence is not obtained.

* * * * *